(12) United States Patent
Reusch et al.

(10) Patent No.: US 11,672,632 B2
(45) Date of Patent: Jun. 13, 2023

(54) MULTI-LAYERED ZIRCONIA DENTAL BLANK WITH REVERSE LAYERS, PROCESS FOR ITS PREPARATION AND USES THEREOF

(71) Applicant: pritidenta GmbH, Leinfelden-Echterdingen (DE)

(72) Inventors: Berthold Reusch, Munich (DE); David Figge, Lorsch (DE)

(73) Assignee: pritidenta GmbH, Leinfelden-Echterdingen (DE)

( * ) Notice: Subject to any disclaimer, the term of this patent is extended or adjusted under 35 U.S.C. 154(b) by 0 days.

(21) Appl. No.: 17/062,992

(22) Filed: Oct. 5, 2020

(65) Prior Publication Data
US 2022/0104925 A1   Apr. 7, 2022

(51) Int. Cl.
| | |
|---|---|
| A61C 13/00 | (2006.01) |
| A61K 6/818 | (2020.01) |
| A61C 13/08 | (2006.01) |
| C04B 35/488 | (2006.01) |
| A61C 13/083 | (2006.01) |

(52) U.S. Cl.
CPC ........ *A61C 13/083* (2013.01); *A61C 13/0004* (2013.01); *A61C 13/0006* (2013.01); *A61C 13/0022* (2013.01); *A61C 13/082* (2013.01); *A61K 6/818* (2020.01); *C04B 35/488* (2013.01); *C04B 2235/3225* (2013.01)

(58) Field of Classification Search
None
See application file for complete search history.

(56) References Cited

U.S. PATENT DOCUMENTS

| | | |
|---|---|---|
| 7,981,531 B2 | 7/2011 | Rheinberger et al. |
| 8,034,264 B2 | 10/2011 | Ritzberger |
| 8,178,012 B1 | 5/2012 | Khan et al. |
| 8,541,329 B2 | 9/2013 | Ritzberger et al. |
| 8,632,889 B2 | 1/2014 | Thiel et al. |
| 8,691,122 B2 | 4/2014 | Rheinberger et al. |
| 8,697,176 B2 | 4/2014 | Wang et al. |
| 8,721,336 B2 | 5/2014 | Rheinberger et al. |
| 8,722,555 B2 | 5/2014 | Yamashita et al. |

(Continued)

FOREIGN PATENT DOCUMENTS

| | | |
|---|---|---|
| EP | 2 024 300 B1 | 2/2009 |
| EP | 3 108 849 B1 | 12/2016 |

(Continued)

OTHER PUBLICATIONS

Translation of KR101601948 B1, via FIT database (Year: 2016).*

*Primary Examiner* — Elizabeth Collister
(74) *Attorney, Agent, or Firm* — Dority & Manning, P.A.

(57) ABSTRACT

The present invention relates to a novel multi-layered zirconia dental blank comprising at least two reverse layers. Further, the invention relates to a process for the preparation of such a multi-layered zirconia dental blank. The invention also relates to the use of such a multi-layered zirconia dental blank for the production of a dental article. Preferred dental articles are artificial teeth, inlays, onlays, bridges, crowns, veneers, facings, crown frameworks, bridged frameworks, implants, abutments, copings or orthodontic appliances. Moreover, the invention relates to a process for producing a dental article out of such a multi-layered zirconia dental blank.

14 Claims, 7 Drawing Sheets

(56) References Cited

U.S. PATENT DOCUMENTS

| | | | |
|---|---|---|---|
| 8,936,848 B2 | 1/2015 | Jung et al. | |
| 9,249,056 B2 | 2/2016 | Fujisaki et al. | |
| 9,249,058 B2 | 2/2016 | Yamashita et al. | |
| 9,649,179 B2 | 5/2017 | Jung et al. | |
| 9,668,837 B2 | 6/2017 | Jung | |
| 9,681,931 B2 | 6/2017 | Thiel et al. | |
| 9,770,311 B2 | 9/2017 | Zipprich et al. | |
| 9,872,746 B2 | 1/2018 | Hauptmann et al. | |
| 9,962,247 B2 | 5/2018 | Fujisaki et al. | |
| 10,004,668 B2 | 6/2018 | Brodking et al. | |
| 10,034,728 B2 | 7/2018 | Jung et al. | |
| 10,039,620 B2 | 8/2018 | Brodbeck et al. | |
| 10,226,313 B2 | 3/2019 | Jung et al. | |
| 10,238,473 B2 | 3/2019 | Jung et al. | |
| 10,292,795 B2 | 5/2019 | Herrmann et al. | |
| 10,327,875 B2 | 6/2019 | Jung | |
| 10,426,583 B2 | 10/2019 | Jung et al. | |
| 10,441,391 B2 | 10/2019 | Volkl et al. | |
| 10,463,457 B2 | 11/2019 | Jung et al. | |
| 10,479,729 B2 | 11/2019 | Valenti et al. | |
| 10,485,640 B2 | 11/2019 | Volkl et al. | |
| 10,550,040 B2 | 2/2020 | Yamauchi et al. | |
| 10,555,795 B2 | 2/2020 | Fujisaki et al. | |
| 10,610,460 B2 | 4/2020 | Brodkin et al. | |
| 10,631,961 B2 | 4/2020 | Jung et al. | |
| 10,703,076 B2 | 7/2020 | Ito et al. | |
| 10,736,717 B2 | 8/2020 | Zipprich | |
| 10,758,326 B2 | 9/2020 | Yamada et al. | |
| 10,799,327 B2 | 10/2020 | Jung et al. | |
| 10,799,328 B2 | 10/2020 | Jung et al. | |
| 10,842,599 B2 | 11/2020 | Volkl et al. | |
| 10,898,302 B2 | 1/2021 | Dittmann et al. | |
| 11,045,292 B2 | 6/2021 | Yamada et al. | |
| 11,051,916 B2 | 7/2021 | Jung et al. | |
| 11,077,646 B2 | 8/2021 | Ito et al. | |
| 11,090,142 B2 | 8/2021 | Volkl et al. | |
| 11,161,789 B2 | 11/2021 | Yang et al. | |
| 2010/0216095 A1 | 8/2010 | Scharf | |
| 2012/0196244 A1 | 8/2012 | Khan et al. | |
| 2012/0214134 A1 | 8/2012 | Khan et al. | |
| 2013/0221554 A1* | 8/2013 | Jung | B32B 18/00 264/16 |
| 2016/0120765 A1* | 5/2016 | Dang | A61K 6/822 428/218 |
| 2016/0157971 A1 | 6/2016 | Rothbrust et al. | |
| 2017/0245970 A1 | 8/2017 | Jung et al. | |
| 2018/0125616 A1* | 5/2018 | Kitamura | C04B 38/0067 |
| 2018/0193118 A1* | 7/2018 | Jung | A61C 13/0006 |
| 2019/0099245 A1 | 4/2019 | Rothbrust et al. | |
| 2019/0231494 A1* | 8/2019 | Dittmann | C04B 38/0054 |
| 2019/0380815 A1 | 12/2019 | Aiba et al. | |
| 2019/0381769 A1 | 12/2019 | Reinshagen et al. | |
| 2020/0030064 A1 | 1/2020 | Volkl et al. | |
| 2020/0113658 A1 | 4/2020 | Ban et al. | |
| 2020/0222287 A1 | 7/2020 | Brodkin et al. | |
| 2020/0283341 A1 | 9/2020 | Ushio et al. | |
| 2020/0289242 A1 | 9/2020 | Correia et al. | |
| 2020/0297464 A1 | 9/2020 | Bohm et al. | |
| 2020/0360114 A1 | 11/2020 | Zipprich | |
| 2021/0137655 A1 | 5/2021 | Shen et al. | |
| 2021/0155551 A1 | 5/2021 | Park | |
| 2021/0196437 A1 | 7/2021 | Seger et al. | |
| 2021/0282907 A1 | 9/2021 | Yamada et al. | |
| 2021/0290351 A1 | 9/2021 | Voelkl et al. | |
| 2022/0098115 A1 | 3/2022 | Yang et al. | |
| 2022/0273403 A1 | 9/2022 | Godiker et al. | |
| 2022/0289632 A1 | 9/2022 | Godiker et al. | |

FOREIGN PATENT DOCUMENTS

| | | | |
|---|---|---|---|
| KR | 101601948 B1 * | 3/2016 | ........... A61C 13/083 |
| WO | WO2007137696 | 12/2007 | |
| WO | WO2014206439 | 12/2014 | |
| WO | WO2022018283 | 1/2022 | |

* cited by examiner

MULTI-LAYERED ZIRCONIA DENTAL BLANK WITH REVERSE LAYERS, PROCESS FOR ITS PREPARATION AND USES THEREOF

FIELD OF THE INVENTION

The present invention relates to a novel multi-layered zirconia dental blank comprising at least two reverse layers. Further, the invention relates to a process for the preparation of such a multi-layered zirconia dental blank. The invention also relates to the use of such a multi-layered zirconia dental blank for the production of a dental article. Preferred dental articles are artificial teeth, inlays, onlays, bridges, crowns, veneers, facings, crown frameworks, bridged frameworks, implants, abutments, copings or orthodontic appliances. Moreover, the invention relates to a process for producing a dental article out of such a multi-layered zirconia dental blank.

BACKGROUND OF THE INVENTION

The use of artificial ceramic materials for dental applications, for example for the production of dental articles, is increasing due to an elevated demand of cosmetic dentistry. The demand for aesthetics in restorative dentistry has risen dramatically in the last few decades. Most patients desire that their restorations resemble natural tooth structure and the colour and translucency of a natural tooth.

A natural tooth does not have a uniform colouring and translucency. Furthermore, each tooth is individual in its three-dimensional form. Therefore, the preparation of dental restorations such as dental bridges requires additionally three-dimensional colouration and translucency. Each artificial tooth should be clearly differentiated from the adjacent tooth by colour. However, the colour gradient within a tooth should be homogeneous from the tooth enamel to the gingival preparation margin (dentin). Enamel is more translucent and less colour intense compared to the dentin. Therefore, the top enamel area of a tooth is looking brighter and more translucent compared to the bottom part of a tooth.

Among others, zirconia ceramic is a popular artificial ceramic material for the preparation of dental restorations. One drawback of the use of zirconia ceramic is the white colour thereof, which does not resemble the colour of a natural tooth. Therefore, several methods for colouring zirconia ceramic have been developed.

Zirconia ceramic may be coloured by means of colouring solutions. A pre-sintered body is milled and coloured by dipping the zirconia ceramic into a colouring solution or by painting the zirconia ceramic with a colouring solution. A disadvantage of this method is that colouring solutions may in general result in significant changes of the microstructure of the zirconia ceramic and may cause unpredictable problems due to decreasing strength of the zirconia ceramic or chipping of the veneering ceramics.

In another method, a multi-coloured zirconia ceramic dental article may be obtained by combining a coloured zirconia ceramic with colouring intermediate layers to resemble the colour and translucency gradient of a natural tooth. A disadvantage of multi-coloured zirconia ceramic dental articles prepared by this method is that boundaries between the different coloured and translucent layers in the final dental restorations remain perceptible by the naked eye.

Multi-layered zirconia blanks which are prepared from several differently coloured layers are known from the state of the art.

For example, EP 2 024 300 B1 describes a method for producing a ceramic, wherein a green body, which consists of at least two different powder mixtures that are compacted to form a moulded body, said powder mixture respectively containing a ceramic powder and a colouring metal compound and/or colouring pigment, wherein each set of two powder mixtures differs in its composition of colouring metal compound and/or colour pigment, is initially produced and subsequently sintered, wherein the ceramics are shaped prior to sintering and/or as an intermediate step, during which sintering is interrupted and then continued after shaping and wherein the at least two powder mixtures have the same volume changes during sintering.

EP 3 108 849 B1 describes dental mill blanks produced by using two different powder compositions being arranged in alternating order. The porous multilayered zirconia dental mill blank comprises a bottom layer B having the composition COMP-B which comprises ceramic components CER-COMP-B, colouring components COL-COMP-B and stabilizing components STAB-COMP-B, a top layer E having the composition COMP-E which comprises ceramic components CER-COMP-E, colouring components COL-COMP-E stabilizing components STAB-COMP-E, at least one intermediate layer E x having the composition COMP-E of top layer E, at least one intermediate layer B x having the composition COMP-B of bottom layer B, x being an integer and indicating the number of intermediate layers, wherein the layers with compositions COMP-B and COMP-E are arranged in alternating order, and wherein the thickness of the individual layers B, B x is decreasing from bottom to top and the thickness of the individual layers E, E x is decreasing from top to bottom.

However, none of the multi-layered zirconia blanks of the state of the art is completely satisfactory for the production of a dental article.

Thus, a need exists for an alternative multi-layered zirconia dental blank that is suitable for the production of a dental article with a smooth colour and translucency gradient closely resembling the colour and translucency gradient of a natural tooth, wherein no colour boundaries or translucency boundaries can be seen in the final dental article with the naked eye. In particular, there is a desire to prepare a dental article having the appearance of a natural tooth in a cost-efficient manner.

SUMMARY OF THE INVENTION

The present invention, in one aspect, relates to a multi-layered zirconia dental blank comprising:

a top layer TL-HT consisting of an yttria-stabilized zirconia powder having the composition TL-HT, a bottom layer BL-ET consisting of an yttria-stabilized zirconia powder having the composition BL-ET, at least two intermediate layers $IL_X$-HT-ET consisting of a mixture of the yttria-stabilized zirconia powders having the compositions TL-HT and BL-ET, X being an integer>1 designating the intermediate layer, wherein the yttria-stabilized zirconia powders TL-HT and BL-ET comprise colouring oxides, and at least two reverse layers $R_Y$, Y being an integer>1 designating the reverse layer, wherein the at least two reverse layers $R_Y$ are arranged in each case as a pair of reverse layers between the top layer TL-HT and the first intermediate layer $IL_1$-HT-ET, and/or between two intermediate layers $IL_X$-HT-ET, and/or between the last intermediate layer $IL_X$-HT-ET and the bottom layer BL-ET, and wherein each of the at least two reverse layers $R_Y$ has the same composition as the layer which is adjacent to the respective other reverse layer $R_Y$.

In one embodiment, the invention relates to a multi-layered zirconia dental blank as defined above, wherein the maximum number of the reverse layers $R_Y$=2+2×number of the intermediate layers $IL_X$-HT-ET.

In one embodiment, the invention relates to a multi-layered zirconia dental blank as defined above, wherein the thickness of the layers is as follows:
top layer TL-HT: from 1 mm to 5 mm,
intermediate layers $IL_X$-HT-ET: from 0.6 to 5 mm,
reverse layers $R_Y$: from 0.6 to 1.2 mm, and
bottom layer BL-ET: from 1 mm to 25 mm.

In another embodiment, the invention relates to a multi-layered zirconia dental blank as defined above, having from 2 to 20 intermediate layers $IL_X$-HT-ET.

In one embodiment, the invention relates to a multi-layered zirconia dental blank as defined above, having from 2 to 44 reverse layers $R_Y$.

In another embodiment, the invention relates to a multi-layered zirconia dental blank as defined above, wherein the yttria-stabilized zirconia powder having the composition HT of the top layer TL-HT contains from 8 wt. % to 30 wt. %, particularly preferred from 8 wt. % to 20 wt. % yttria, and
the yttria-stabilized zirconia powder having the composition ET of the bottom layer BL-ET contains from 2 wt. % to 15 wt. %, preferably from 2 wt. % to 10 wt. %, particularly preferred from 4 wt. % to 8 wt. % yttria.

In one embodiment, the invention relates to a multi-layered zirconia dental blank as defined above, wherein the zirconia dental blank comprises a reverse layer $R_1$ having the same composition as intermediate layer $IL_1$-HT-ET, and a reverse layer $R_2$ having the same composition as the top layer TL-HT.

In another embodiment, the invention relates to a multi-layered zirconia dental blank as defined above, wherein the zirconia dental blank comprises a reverse layer $R_Y$ having the same composition as the bottom layer BL-ET, and a reverse layer $R_{Y+1}$ having the same composition as the last intermediate layer $IL_X$-HT-ET.

In one embodiment, the invention relates to a multi-layered zirconia dental blank as defined above, having the following seven layers arranged one on top of the other:
Layer 1: top layer TL-HT,
Layer 2: intermediate layer $IL_1$-HT-ET,
Layer 3: intermediate layer $IL_2$-HT-ET,
Layer 4: intermediate layer $IL_3$-HT-ET,
Layer 5: reverse layer $R_1$ having the composition BL-ET,
Layer 6: reverse layer $R_2$ having the composition $IL_3$-HT-ET, and Layer
7: bottom layer BL-ET.

In another embodiment, the invention relates to a multi-layered zirconia dental blank as defined above, having the following ten layers arranged one on top of the other:
Layer 1: top layer TL-HT,
Layer 2: reverse layer $R_1$ having the composition $IL_1$-HT-ET,
Layer 3: reverse layer $R_2$ having the composition TL-HT,
Layer 4: intermediate layer $IL_1$-HT-ET,
Layer 5: reverse layer $R_3$ having the composition $IL_2$-HT-ET,
Layer 6: reverse layer $R_4$ having the composition $IL_1$-HT-ET;
Layer 7: intermediate layer $IL_2$-HT-ET,
Layer 8: reverse layer $R_5$ having the composition BL-ET,
Layer 9: reverse layer $R_6$ having the composition $IL_2$-HT-ET, and Layer
10: bottom layer BL-ET.

In one embodiment, the invention relates to a multi-layered zirconia dental blank as defined above, having the following thirteen layers arranged one on top of the other:
Layer i: top layer TL-HT,
Layer 2: reverse layer $R_1$ having the composition $IL_1$-HT-ET,
Layer 3: reverse layer $R_2$ having the composition TL-HT,
Layer 4: intermediate layer $IL_1$-HT-ET,
Layer 5: reverse layer $R_3$ having the composition $IL_2$-HT-ET,
Layer 6: reverse layer $R_4$ having the composition $IL_1$-HT-ET;
Layer 7: intermediate layer $IL_2$-HT-ET,
Layer 8: reverse layer $R_5$ having the composition $IL_3$-HT-ET,
Layer 9: reverse layer $R_6$ having the composition $IL_2$-HT-ET,
Layer 10: intermediate layer $IL_3$-HT-ET,
Layer 11: reverse layer $R_7$ having the composition BL-ET,
Layer 12: reverse layer $R_8$ having the composition $IL_3$-HT-ET, and Layer
13: bottom layer BL-ET.

In another embodiment, the invention relates to a multi-layered zirconia dental blank as defined above, wherein the at least two reverse layers $R_Y$ interrupt the gradients of colour (L*a*b*), translucency, strength and yttria content within the main layers TL-HT and BL-ET and the intermediate layers $IL_X$-HT-ET.

In one embodiment, the invention relates to a multi-layered zirconia dental blank as defined above, wherein the colour becomes more intense (gradient of colour) and the translucency decreases (gradient of translucency) from the top layer TL-HT to the bottom layer BL-ET within the intermediate layers $IL_X$-HT-ET, being interrupted by the at least two reverse layers $R_Y$.

In another embodiment, the invention relates to a multi-layered zirconia dental blank as defined above, wherein the yttria content increases (gradient of yttria), and the strength decreases (gradient of strength) from the bottom layer BL-ET to the top layer TL-HT within the intermediate layers $IL_X$-HT-ET, being interrupted by the at least two reverse layers $R_Y$.

In another aspect, the invention relates to a process for the preparation of a multi-layered zirconia dental blank as defined above, comprising the steps of:
(a) putting the yttria-stabilized zirconia powder having the composition ET, the mixtures of the yttria-stabilized zirconia powder having the compositions $IL_X$-HT-ET, and the yttria-stabilized zirconia powder having the composition HT in layers on top of the other, or in reverse order,
(b) pressing the yttria-stabilized zirconia powder layers to a green body, and
(c) pre-firing the green body to obtain the multi-layered zirconia dental blank.

In another aspect, the invention relates to the use of a multi-layered zirconia dental blank as defined above for the production of a dental article, preferably for the production of artificial teeth, inlays, onlays, bridges or crowns, veneers, facings, crown frameworks, bridged frameworks, implants, abutments, copings or orthodontic appliances.

In another aspect, the invention relates to a process for producing a dental article, comprising the steps of:
(a) providing a multi-layered zirconia dental blank as defined above, (b) machining a pre-fired dental article out of the multi-layered zirconia dental blank as defined above, and
(c) sintering the pre-fired dental article to obtain the dental article.

In one embodiment, the invention relates to the process as defined above, wherein the production of the dental article is computer-aided, in particular by means of CAD/CAM methods.

DETAILED DESCRIPTION OF THE INVENTION

Definitions

Figure 1:
FIG. 1 shows a schematic view of a multi-layered dental zirconia blank of the invention as described herein with 13 layers, i.e. with a top layer TL-HT, 3 intermediate layers $IL_X$-HT-ET, 8 reverse layers $R_Y$ and a bottom layer BL-ET and as carried out in Example 3.1.

As used herein, including the accompanying claims, the terms, which are collectively used, have the following meanings.

As used herein, the term "dental application" means any application or use in the dental or orthodontic field, especially a dental restoration, a preform, e.g. a dental milling block or dental blank, a disc or a prefab for application in dental clinics (Chair side) or in dental laboratories.

As used herein, the term "dental article" means any article which can or is to be used in the dental or orthodontic field, especially for producing of or as dental restoration, a tooth model and parts thereof. Examples of dental articles include but are not limited to crowns, bridges, inlays, onlays, veneers, facings, copings, crown frameworks, bridged frameworks, implants, abutments, orthodontic appliances (e.g. brackets, buccal tubes, cleats and buttons) and parts thereof. A dental article should not contain components which are detrimental to the patient's health and thus be free of hazardous and toxic components being able to migrate out of the dental article.

As used herein, the term "dental restoration" means any dental restorative material used to restore the function, integrity and morphology of missing tooth structure.

As used herein, the term "preform" means any piece of a material, which has been preformed for further use, e.g. for use in a dental CAD/CAM machine, especially a dental milling block, a disc or a prefab.

As used herein, the term "dental milling block" or "dental blank" means a solid block (3-dim article) of a material from which a dental article or a dental restoration can or is to be machined.

As used herein, the term "top layer" means the uppermost layer of the multi-layered zirconia dental blank, having a colour resembling the top enamel area of a tooth.

As used herein, the term "top of the dental article" means the part of the dental article having a colour resembling the top enamel area of a tooth.

As used herein, the term "bottom layer" means the lowest layer of the multi-layered zirconia dental blank, having a colour resembling the dentin or cervical part of a tooth.

As used herein, the term "bottom of the dental article" means the part of the dental article having a colour resembling the dentin or cervical part of a tooth, close to the gingiva.

As used herein, the term "intermediate layer" means a layer between the top layer and the bottom layer of the multi-layered zirconia dental blank.

As used herein, the term "reverse layer" means a layer between the top layer and the bottom layer of the multi-layered zirconia dental blank. The reverse layers are arranged in each case as a pair. A reverse layer is a layer that interrupts the gradients within the multi-layered zirconia dental blank, e.g. the gradient of colour, the gradient of translucency, the gradient of yttria, the gradient of strength within the intermediate layers.

As used herein, the term "a pair of reverse layers" means two reverse layers on top of each other. The multi-layered zirconia dental blank may also comprise several pairs of reverse layers directly on top of each other, e.g. four, six, eight, ten or more reverse layers on top of each other. In a preferred embodiment, the multi-layered zirconia dental blank of the invention comprises one or several pairs of two reverse layers.

As used herein, the term "disc" means a disc (3-dim article) of a material from which a dental article or a dental restoration can or is to be machined.

As used herein, the term "prefab" means any preformed body resembling the tooth geometry.

As used herein, the term "powder" means a dry, bulk composed of a large number of fine particles that may flow freely when shaken or tilted. In a preferred embodiment, the powder is a powder batch.

As used herein, the terms "colour" and "coloured" relate to the colour, brightness and translucency of a material, body or layer. According to the invention the terms "color" and "coloured" relate in particular to brightness. Changes in colour are therefore understood to include in particular changes in brightness.

Colours can for example be characterized by their Lab value also known as CIE L*a*b. The CIELAB color space is a color space defined by the International Commission on Illumination (CIE) in 1976. Alternatively, colours may be characterized by a colour code commonly used in the dental industry. Examples of such colour codes are the Vitapan Classical® and the Vita 3D Master®, both from VITA Zahnfabrik H. Rauter GmbH & Co. KG, and Ivoclar Vivadent AG's Chromascop®. For example, the term "VITA dental color(s)" means the gradual 16 VITA classical A1-D4 shade guide serving to accurately determining tooth shade and the 32 3D-master shade guide VITA basic colors. The arrangement of the shades in the VITA classical family of shades is as follows: A1, A2, A3, A3.5, A4 (reddish-brownish), B1, B2, B3, B4 (reddish-yellowish), C1, C2, C3, C4 (greyish shades), D2, D3, D4 (reddish-grey).

As used herein, the term "translucency" is the light-transmitting capacity of a material, for example of a blank or a dental article, i.e. the ratio of transmitted to incident light intensity.

As used herein, the term "machining" is means milling, grinding, cutting, carving, or shaping a material by a machine. Milling is usually faster and more cost effective than grinding. A "machinable article" is an article having a 3-dimensional shape and having sufficient strength to be machined.

Multi-Layered Zirconia Dental Blank with Reverse Layers of the Invention

As indicated above, there is a need for an alternative multi-layered zirconia dental blank that is suitable for the production of a dental article with a smooth colour and translucency gradient closely resembling the colour and translucency gradient of a natural tooth, wherein no colour boundaries or translucency boundaries can be seen in the final dental article with the naked eye. In particular, there is a desire to prepare a dental article having the appearance of a natural tooth in a cost-efficient manner. Furthermore, there is a need for multi-layered zirconia dental blanks with new layering concepts.

Thus, a problem of the invention is to provide an alternative multi-layered zirconia dental blank that is suitable for the production of a dental article wherein no colour boundaries or translucency boundaries can be seen in the final dental article with the naked eye.

It has now been found that this problem is surprisingly solved by a multi-layered zirconia dental blank comprising:

a top layer TL-HT consisting of an yttria-stabilized zirconia powder having the composition TL-HT, a bottom layer BL-ET consisting of an yttria-stabilized zirconia powder having the composition BL-ET, at least two intermediate layers $IL_X$-HT-ET consisting of a mixture of the yttria-stabilized zirconia powders having the compositions TL-HT and BL-ET, X being an integer>1 designating the intermediate layer, wherein the yttria-stabilized zirconia powders TL-HT and BL-ET comprise colouring oxides, and at least two reverse layers $R_Y$, Y being an integer>1 designating the reverse layer, wherein the at least two reverse layers $R_Y$ are arranged in each case as a pair of reverse layers between the top layer TL-HT and the first intermediate layer $IL_1$-HT-ET, and/or between two intermediate layers $IL_X$-HT-ET, and/or between the last intermediate layer $IL_X$-HT-ET and the bottom layer BL-ET, and wherein each of the at least two reverse layers $R_Y$ has the same composition as the layer which is adjacent to the respective other reverse layer $R_Y$.

Preferably, the maximum number of the reverse layers $R_Y$=2+2×number of the intermediate layers $IL_X$-HT-ET.

Specifically, it has been found that by including at least two reverse layers $R_Y$ as a pair of reverse layers into the multi-layered zirconia dental blank, wherein each of the at least two reverse layers $R_Y$ has the same composition as the layer which is adjacent to the respective other reverse layer $R_Y$, the gradient of colour, the gradient of translucency the gradient of yttria, the gradient of strength within the intermediate layers are interrupted and reversed.

This means that the gradient of colour, the gradient of translucency, the gradient of yttria content, the gradient of strength within each pair of reverse layers $R_Y$ has a direction which is contrary to the direction of colour, translucency, yttria content and strength between the top layer TL-HT and the bottom layer BL-ET within the intermediate layers $IL_X$-HT-ET.

Thus, in one embodiment the invention relates to a multi-layered zirconia dental blank as described herein, wherein the at least two reverse layers $R_Y$ interrupt the gradients of colour (L*a*b*), translucency, strength and yttria content within the main layers TL-HT and BL-ET and the intermediate layers $IL_X$-HT-ET.

In the multi-layered zirconia dental blank of the invention as described herein, the colour becomes more intense (gradient of colour) and the translucency decreases (gradient of translucency) from the top layer TL-HT to the bottom layer BL-ET within the intermediate layers $IL_X$-HT-ET, being interrupted by the at least two reverse layers $R_Y$. Further, the yttria content increases (gradient of yttria), and the strength decreases (gradient of strength) from the bottom layer BL-ET to the top layer TL-HT within the intermediate layers $IL_X$-HT-ET, being interrupted by the at least two reverse layers $R_Y$.

The multi-layered zirconia dental blank of the invention as described herein is characterized by the gradients as described herein. However, the gradients are only visible with the naked eye, if at all in a dental article produced from the multi-layered zirconia dental blank of the invention.

Unexpectedly, the at least two reverse layers $R_Y$ described herein conceal the perceptible boundaries of the intermediate layers in the final multi-coloured zirconia ceramic, i.e. in the dental article.

Surprisingly, a dental article produced from the multi-layered zirconia dental blank as described herein does not show any colour or translucency boundaries perceptible with the naked eye between the different layers.

Thus, the layering concept of the multi-layered zirconia dental blank of the invention is suitable for the production of an aesthetic dental article with a color gradient closely resembling a natural tooth.

The at least two reverse layers $R_Y$ may be arranged between the top layer TL-HT and the first intermediate layer $IL_1$-HT-ET, and/or between two intermediate layers $IL_X$-HT-ET, and/or between the last intermediate layer $IL_X$-HT-ET and the bottom layer BL-ET.

In one embodiment, two reverse layers $R_Y$ are arranged between the last intermediate layer $IL_X$-HT-ET and the bottom layer BL-ET.

In another embodiment two reverse layers $R_Y$ are arranged between the top layer TL-HT and the first intermediate layer $IL_1$-HT-ET.

A multi-layered zirconia dental blank of the invention may have a total height of from 8 mm to 45 mm, particularly preferred from 10 mm to 30 mm.

The thickness of the top layer TL-HT ranges from 1 mm to 5 mm, e.g. from 1 mm to 4 mm, from 1.5 mm to 4 mm, from 2 mm to 3.5 mm, from 2.5 mm to 3.5 mm or from 2.5 to 3.0 mm.

The thickness of the intermediate layers $IL_X$-HT-ET ranges from 0.6 to 5 mm, e.g. from 0.7 mm to 4.9 mm, from 0.8 mm to 4.9 mm, from 0.8 mm to 4.8 mm, from 0.8 mm to 4.7 mm, from 0.8 mm to 4.6 mm, from 0.8 mm to 4.5 mm, from 0.8 mm to 4.4 mm, from 0.8 mm to 4.3 mm, from 0.8 mm to 4.2 mm, from 0.8 mm to 4.1 mm, from 0.8 mm to 4.0 mm, from 0.8 mm to 3.9 mm, from 0.8 mm to 3.8 mm, from 0.8 mm to 3.7 mm, from 0.8 mm to 3.6 mm, from 0.8 mm to 3.5 mm, from 0.8 mm to 3.4 mm, from 0.8 mm to 3.3 mm, from 0.8 mm to 3.2 mm, from 0.8 mm to 3.1 mm, from 0.8 mm to 3.0 mm, from 0.8 mm to 2.5 mm, from 0.8 mm to 2.0 mm, from 0.8 mm to 1.5 mm, from 0.8 mm to 1.3 mm, from 0.8 mm to 1.2 mm, from 0.8 mm to 1.1 mm, or from 0.8 mm to 1.0 mm, particularly preferred from 0.8 mm to 3.0 mm. The thickness of the intermediate layers $IL_X$-HT-ET may be the same or different.

The thickness of the different intermediate layers $IL_X$-HT-ET, e.g. of intermediate layers $IL_1$-HT-ET, intermediate layer $IL_2$-HT-ET, intermediate layer $IL_3$-HT-ET etc. may be the same or different.

The thickness of the reverse layers $R_Y$ ranges from 0.6 to 1.2 mm, e.g. from 0.65 to 1.2 mm, from 0.7 mm to 1.2 mm, from 0.65 to 1.1 mm, from 0.7 mm to 1.1 mm, from 0.75 mm to 1.0 mm, or from 0.8 mm to 0.9 mm, particularly preferred from 0.6 mm to 0.8 mm. The thickness of the reverse layers $R_Y$ may be the same or different. In a preferred embodiment, the two reverse layers $R_Y$ forming a pair of reverse layers $R_Y$ have the same thickness.

The thickness of the different reverse layers $R_Y$, e.g. of reverse layers $R_1$, $R_2$, $R_3$ etc., may be the same or different.

The thickness of two reverse layers $R_Y$ in a pair of reverse layers may be the same or different.

The thickness of the intermediate layers $IL_X$-HT-ET and of the reverse layers $R_Y$ may be the same or different.

The thickness of the bottom layer BL-ET ranges from 1 mm to 25 mm, e.g. from 1 mm to 25 mm, from 2 mm to 25 mm, from 3 mm, to 25 mm, from 4 mm to 25 mm, from 5 mm to 25 mm, from 6 mm to 20 mm, from 6 mm to 18 mm, from 6 mm to 16 mm, from 6 mm to 14 mm, from 6.5 mm to 19 mm, from 7 mm to 18 mm, from 7.5 mm to 17 mm, from 8 mm to 16 mm, from 8 mm to 15 mm, from 8 mm to 14 mm, from 8 mm to 13 mm, from 8 mm to 12 mm, from 8 mm to 11 mm.

In one embodiment, in the multi-layered zirconia dental blank as defined above, the thickness of the layers is as follows:
top layer TL-HT: from 1 mm to 5 mm,
intermediate layers $IL_X$-HT-ET: from 0.6 to 5 mm,
reverse layers $R_Y$: from 0.6 to 1.2 mm, and
bottom layer BL-ET: from 1 mm to 25 mm.

In one embodiment, in the multi-layered zirconia dental blank as defined above, the thickness of the layers is as follows:
top layer TL-HT: from 1 mm to 5 mm,
intermediate layers $IL_X$-HT-ET: from 0.6 to 5 mm,
reverse layers $R_Y$: from 0.6 to 1.2 mm, and
bottom layer BL-ET: from 5 mm to 25 mm.

In a preferred embodiment, in the multi-layered zirconia dental blank as defined above, the thickness of the layers is as follows:
top layer TL-HT: from 1 mm to 4 mm,
intermediate layers $IL_X$-HT-ET: from 0.8 to 4 mm,
reverse layers $R_Y$: from 0.6 to 1.0 mm, and
bottom layer BL-ET: from 6 mm to 20 mm.

In a preferred embodiment, in the multi-layered zirconia dental blank as defined above, the thickness of the layers is as follows:
top layer TL-HT: from 1 mm to 4 mm,
intermediate layers $IL_X$-HT-ET: from 0.8 to 4 mm,
reverse layers $R_Y$: from 0.7 to 1.2 mm, and
bottom layer BL-ET: from 6 mm to 20 mm.

In a preferred embodiment, in the multi-layered zirconia dental blank as defined above, the thickness of the layers is as follows:
top layer TL-HT: from 1 mm to 4 mm,
intermediate layers $IL_X$-HT-ET: from 0.8 to 3 mm,
reverse layers $R_Y$: from 0.7 to 0.9 mm, and
bottom layer BL-ET: from 6 mm to 14 mm.

In a preferred embodiment, in the multi-layered zirconia dental blank as defined above, the thickness of the layers is as follows:
top layer TL-HT: from 1 mm to 4 mm,
intermediate layers $IL_X$-HT-ET: from 0.8 to 4 mm,
reverse layers $R_Y$: from 0.8 to 1.0 mm, and
bottom layer BL-ET: from 6 mm to 20 mm.

If the multi-layered zirconia dental blank has the shape of a block, the dental blank has typically the following dimensions:
x-dimension (L): from 30 to 45 mm, or from 35 to 40 mm,
y-dimension (W): from 10 to 30 mm, or from 15 to 25 mm,
z-dimension (H): from 8 to 45 mm, or from 10 to 30 mm.

If the multi-layered zirconia dental blank has the shape of a disc, the dental mill blank has typically the following dimensions:
Diameter: from 90 mm to 110 mm, or from 95 to 100 mm, and height: from 8 to 45 mm, particularly preferred from 10 mm to 30 mm.

Between the top layer TL-HT and the bottom layer BL-ET there are at least two intermediate layers $IL_X$-HT-ET.

A further advantage of the multi-layered zirconia dental blank of the invention is that multiple layers with different compositions can be created based on only two different types of coloured yttria-stabilized zirconia powders, i.e. powder compositions.

Bottom layer "BL-ET" means that the bottom layer consists to 100% of the 5 powder composition ET.

Top layer "TL-HT" means that the top layer consists to 100% of the powder composition HT.

In the multi-layered zirconia dental blank as described herein, the yttria-stabilized zirconia powder having the composition HT of the top layer TL-HT contains from 8 wt. % to 30 wt. %, particularly preferred from 8 wt. % to 20 wt. % yttria, e.g. from 8 wt. % to 20 wt. %, from 8 wt. % to 18 wt. %, from 8 wt. % to 16 wt. %, or from 8 wt. % to 15 wt. % yttria. In a preferred embodiment, the powder composition HT 15 contains from 8 wt. % to 15 wt. % yttria.

In the multi-layered zirconia dental blank as described herein, the yttria-stabilized zirconia powder having the composition ET of the bottom layer BL-ET contains from 2 wt. % to 15 wt. %, preferably from 2 wt. % to 10 wt. %, particularly preferred 20 from 4 wt. % to 8 wt. % yttria.

The composition of the powder compositions ET and HT is shown in Table 1 below:

TABLE 1

Composition of the powder compositions ET and HT

| Component | Powder composition ET Content of component (wt. %) | Powder composition HT Content of component (wt. %) |
|---|---|---|
| Main crystal phase | Tetragonal, Tetragonal/cubic | Tetragonal/cubic |
| $ZrO_2$ + $HfO_2$ + $Y_2O_3$ + $Al_2O_3$ | (>99.9) | (>99.9) |
| $HfO_2$ | <3 | <3 |
| $Y_2O_3$ (stabilizing crystal phase) | 4.65-7.95 (3-4 mol %) | 8.55-10.11 (5 mol %) |
| $Al_2O_3$ | <0.1 | <0.1 |
| $SiO_2$ | <0.02 | <0.02 |
| $Fe_2O_3$ (incl. coloring component) | <0.12 | <0.12 |
| $Er_2O_3$ (coloring component) | 0-0.6 | 0-0.6 |
| $Co_3O_4$ or $MnO_2$ (coloring component) | 0.00007 | 0.00007 |
| $ZrO_2$ | Remainder 88.1-92.25 | Remainder 85.9-88.35 |

As shown in Table 1, the multi-layered zirconia dental blank of the invention does not comprise one or more of the following elements/components: glass or glass ceramic; oxides of Si, K, Na in an amount above 1 wt. % with respect to the 5 weight of the multi-layered zirconia dental blank.

The compositions HT and ET may contain a fluorescing agent commonly used in dental materials.

The yttria-stabilized zirconia powders having the compositions HT and ET are based on yttria-stabilized zirconia powders of the manufacturer Tosoh as described in the Technical Data Sheet Zpex® (3 mol % Yttria stabilized zirconia), Zpex®4 (4 mol % Yttria stabilized zirconia), e.g. as of Mar. 16, 2020 as possible powders for ET and Zpex® smile (5 mol % Yttria stabilized zirconia), as possible powder for HT. The zirconia oxide powders consist of zirconium dioxide ($ZrO_2$, also designated as "zirconium oxide") that is stabilized by the addition of amounts of yttrium oxide ($Y_2O_3$, "yttria, yttrium"). As a result of the addition of yttrium oxide, yttria-stabilized tetragonal and cubic zirconium oxide is obtained.

The different tooth-like colours of the multi-layered zirconia dental blank are created by adding the following metal oxides to the powder compositions ET and HT, wherein the total amount of the metal oxides is less than 0.7 wt. %.

yellow: $Fe_2O_3$ (0.035-0.12 wt. %)
pink: $Er_2O_3$ (0.0%-0.6 wt. %)
grey: $Co_2O_3$ or $MnO_2$ (<0.00007 wt. %).

x is an integer>1 designating the intermediate layer $IL_X$-HT-ET.

"HT-ET" means that the intermediate layer $IL_X$-HT-ET consists of a mixture of the powder compositions HT and ET. For example, intermediate layer $IL_1$-HT-ET is the first intermediate layer after the top layer TL-HT and consists of a mixture of the powder compositions HT and ET.

The multi-layered zirconia dental blank of the invention may have from 2 to 20 intermediate layers $IL_X$-HT-ET, e.g. from 2 to 10 intermediate layers $IL_X$-HT-ET, from 2 to 8 intermediate layers $IL_X$-HT-ET, from 2 to 6 intermediate layers $IL_X$-HT-ET, in particular from 2 to 4 intermediate layers $IL_X$-HT-ET, and particularly preferred 2 to 3 intermediate layers.

Y is an integer>1 designating the reverse layer $R_Y$.

Moreover, the chemical composition of the reverse layers $R_Y$ is designated as follows:

"$R_Y$-TL-HT" means that the reverse layer $R_Y$ has the same composition as the top layer and consists of the powder composition HT.

"$R_Y$-$IL_X$-HT-ET" means that the reverse layer $R_Y$ has the same composition as the intermediate layer $IL_X$-HT-ET and consists of the same mixture of the powder compositions HT and ET as intermediate layer $IL_X$. For example, $R_6$-$IL_2$-HT-ET is the sixth reverse layer after the top layer having the same composition as intermediate layer $IL_2$-HT-ET. As to the powder composition, e.g. 33% TL-HT+67% BL-ET means that the powder composition of e.g. $R_6$-$IL_2$-HT-ET contains 33% of the powder composition HT and 67% of the powder composition ET.

"$R_Y$-BL-ET" means that the reverse layer $R_Y$ has the same composition as the bottom layer and consists of the powder composition ET.

The maximum number of the reverse layers can be calculated by the following formula:

$R_Y$=2+2×number of the intermediate layers $IL_X$-HT-ET.

For example, if the number of intermediate layers $IL_X$-HT-ET is 2, the maximum number of the reverse layers $R_Y$=2+2×2=6.

The multi-layered zirconia dental blank of the invention may have from 2 to 44 reverse layers $R_Y$, e.g. from 2 to 40 reverse layers $R_Y$, from 2 to 36 reverse layers $R_Y$, from 2 to 30 reverse layers $R_Y$, from 2 to 28 reverse layers $R_Y$, from 2 to 26 reverse layers $R_Y$, from 2 to 24 reverse layers $R_Y$, from 2 to 22 reverse layers $R_Y$, from 2 to 20 reverse layers $R_Y$, from 2 to 18 reverse layers $R_Y$, from 2 to 16 reverse layers $R_Y$, from 2 to 14 reverse layers $R_Y$, from 2 to 12 reverse layers $R_Y$, from 2 to 10 reverse layers $R_Y$, from 2 to 8 reverse layers $R_Y$, from 2 to 6 reverse layers $R_Y$, or from 2 to 4 reverse layers $R_Y$. In a preferred embodiment the multilayered zirconia dental blank of the invention has 2, 6 or 8 reverse layers $R_Y$.

The layering of the multi-layered zirconia dental blank of the invention may be based on the layering of the colour codes common in the dental industry, such as the Vitapan Classical® or the Vita 3D Master®, both from VITA Zahnfabrik H. Rauter GmbH & Co. KG, or Ivoclar Vivadent AG's Chromascop®. The tooth models of these colour codes in each case define only one colour, but similar to teeth are built up of layers of different material mixtures and/or colours and/or translucencies, and are based on the different colors of human teeth.

This basic colour allocation is also applied in the multi-layered zirconia dental blank of the invention, with the result that the dental article produced from the multi-layered zirconia dental blank of the invention correspond very closely to the natural tooth.

In a preferred embodiment, the multi-layered zirconia dental blank of the invention comprises a reverse layer $R_1$ having the same composition as intermediate layer $IL_1$-HT-ET, and a reverse layer $R_2$ having the same composition as the top layer TL-HT.

In an alternative embodiment, the multi-layered zirconia dental blank of the invention comprises a reverse layer $R_Y$ having the same composition as the bottom layer BL-ET, and a reverse layer $R_{Y+1}$ having the same composition as the last intermediate layer $IL_X$-HT-ET.

In one embodiment (exemplified in Example 1), the multi-layered zirconia dental blank of the invention has seven layers arranged one on top of the other with 3 intermediate layers and 2 reverse layers:

Layer 1: top layer TL-HT, having a thickness from 1 mm to 5 mm,

Layer 2: intermediate layer $IL_1$-HT-ET, having a thickness from 0.6 mm to 3 mm, Layer 3: intermediate layer $IL_2$-HT-ET, having a thickness from 0.6 mm to 3 mm, Layer 4: intermediate layer $IL_3$-HT-ET, having a thickness from 0.6 mm to 3 mm, Layer 5: reverse layer $R_1$ having the composition BL-ET, having a thickness from 0.6 mm to 1.2 mm, Layer 6: reverse layer $R_2$ having the composition $IL_3$-HT-ET, having a thickness from 0.6 mm to 1.2 mm, and Layer 7: bottom layer BL-ET, having a thickness from 1 mm to 25 mm.

In another embodiment (exemplified in Example 1), the multi-layered zirconia dental blank of the invention has seven layers arranged one on top of the other with 3 intermediate layers and 2 reverse layers:

Layer 1: top layer TL-HT, having a thickness from 1 mm to 5 mm,

Layer 2: intermediate layer $IL_1$-HT-ET, having a thickness from 0.8 mm to 3 mm, Layer 3:

intermediate layer $IL_2$-HT-ET, having a thickness from 0.8 mm to 3 mm, Layer 4:

intermediate layer $IL_3$-HT-ET, having a thickness from 0.8 mm to 3 mm, Layer 5: reverse layer $R_1$ having the composition BL-ET, having a thickness from 0.8 mm to 1.2 mm, Layer 6: reverse layer $R_2$ having the composition $IL_3$-HT-ET, having a thickness from 0.8 mm to 1.2 mm, and Layer 7: bottom layer BL-ET, having a thickness from 5 mm to 25 mm.

In a particular preferred embodiment, (exemplified in Example 1), the layers have the following compositions:

Layer 1: top layer TL-HT, 100% TL-HT
Layer 2: intermediate layer $IL_1$-HT-ET, 75% TL-HT+ 25% BL-ET
Layer 3: intermediate layer $IL_2$-HT-ET, 50% TL-HT+ 50% BL-ET
Layer 4: intermediate layer $IL_3$-HT-ET, 25% TL-HT+ 75% BL-ET
Layer 5: reverse layer $R_1$ having the composition BL-ET, 100% BL-ET
Layer 6: reverse layer $R_2$ having the composition $IL_3$-HT-ET, 25% TL-HT+75% BL-ET and
Layer 7: bottom layer BL-ET, 100% BL-ET.

In a more preferred embodiment (exemplified in Example 1), the seven layers have the following compositions and thicknesses:

| Designation of the layer | Thickness (mm) | Composition of the powder composition |
| --- | --- | --- |
| TL-HT - top layer | 1-5 mm | 100% TL-HT |
| IL1-HT-ET - intermediate layer 1 | 0.6-3 mm | 75% TL-HT + 25% BL-ET |
| IL2-HT-ET - intermediate layer 2 | 0.6-3 mm | 50% TL-HT + 50% BL-ET |
| IL3-HT-ET - intermediate layer 3 | 0.6-3 mm | 25% TL-HT + 75% BL-ET |
| R1-BL-ET - reverse layer 1 | 0.6-1.2 mm | 100% BL-ET |
| R2-IL3-HT-ET - reverse layer 2 | 0.6-1.2 mm | 25% TL-HT + 75% BL-ET |
| BL-ET - bottom layer | 1-25 mm | 100% BL-ET |

In another more preferred embodiment (exemplified in Example 1), the seven 10 layers have the following compositions and thicknesses:

| Designation of the layer | Thickness (mm) | Composition of the powder composition |
| --- | --- | --- |
| TL-HT - top layer | 1-5 mm | 100% TL-HT |
| IL1-HT-ET - intermediate layer 1 | 0.8-3 mm | 75% TL-HT + 25% BL-ET |
| IL2-HT-ET - intermediate layer 2 | 0.8-3 mm | 50% TL-HT + 50% BL-ET |
| IL3-HT-ET - intermediate layer 3 | 0.8-3 mm | 25% TL-HT + 75% BL-ET |
| R1-BL-ET - reverse layer 1 | 0.8-1.2 mm | 100% BL-ET |
| R2-IL3-HT-ET - reverse layer 2 | 0.8-1.2 mm | 25% TL-HT + 75% BL-ET |
| BL-ET - bottom layer | 5-25 mm | 100% BL-ET |

In another embodiment (exemplified in Example 2), the multi-layered zirconia dental blank of the invention has ten layers arranged one on top of the other with 15 2 intermediate layers and 6 reverse layers:

Layer 1: top layer TL-HT, having a thickness from 1 mm to 5 mm,
Layer 2: reverse layer $R_1$ having the composition $IL_1$-HT-ET, having a thickness from 0.6 mm to 1.2 mm,
Layer 3: reverse layer $R_2$ having the composition TL-HT, having a thickness from 0.6 mm to 1.2 mm,
Layer 4: intermediate layer $IL_1$-HT-ET, having a thickness from 0.6 mm to 3 mm, Layer 5: reverse layer $R_3$ having the composition $IL_2$-HT-ET, having a thickness from 0.6 mm to 1.2 mm,
Layer 6: reverse layer $R_4$ having the composition $IL_1$-HT-ET, having a thickness from 0.6 mm to 1.2 mm,
Layer 7: intermediate layer $IL_2$-HT-ET, having a thickness from 0.6 mm to 3 mm, Layer 8: reverse layer $R_5$ having the composition BL-ET, having a thickness from 0.6 mm to 1.2 mm,
Layer 9: reverse layer $R_6$ having the composition $IL_2$-HT-ET, having a thickness from 0.6 mm to 1.2 mm, and
Layer 10: bottom layer BL-ET, having a thickness from 1 mm to 25 mm.

In another embodiment (exemplified in Example 2), the multi-layered zirconia dental blank of the invention has ten layers arranged one on top of the other with 2 intermediate layers and 6 reverse layers:

Layer 1: top layer TL-HT, having a thickness from 1 mm to 5 mm,
Layer 2: reverse layer $R_1$ having the composition $IL_1$-HT-ET, having a thickness from 0.8 mm to 1.2 mm,
Layer 3: reverse layer $R_2$ having the composition TL-HT, having a thickness from 0.8 mm to 1.2 mm,
Layer 4: intermediate layer $IL_1$-HT-ET, having a thickness from 0.8 mm to 3 mm, Layer 5: reverse layer $R_3$ having the composition $IL_2$-HT-ET, having a thickness from 0.8 mm to 1.2 mm,
Layer 6: reverse layer $R_4$ having the composition $IL_1$-HT-ET, having a thickness from 0.8 mm to 1.2 mm,
Layer 7: intermediate layer $IL_2$-HT-ET, having a thickness from 0.8 mm to 3 mm, Layer 8: reverse layer $R_5$ having the composition BL-ET, having a thickness from 0.8 mm to 1.2 mm,
Layer 9: reverse layer $R_6$ having the composition $IL_2$-HT-ET, having a thickness from 0.8 mm to 1.2 mm, and
Layer 10: bottom layer BL-ET, having a thickness from 5 mm to 25 mm.

In a particular preferred embodiment, (exemplified in Example 2), the layers have the following powder compositions:

Layer 1: top layer TL-HT, 100% TL-HT
Layer 2: reverse layer $R_1$ having the composition $IL_1$-HT-ET, 67% TL-HT+33% 5 BL-ET,
Layer 3: reverse layer $R_2$ having the composition TL-HT, 100% TL-HT Layer 4: intermediate layer $IL_1$-HT-ET,
Layer 5: reverse layer $R_3$ having the composition $IL_2$-HT-ET, 67% TL-HT+33% BL-ET, Layer 6: reverse layer $R_4$ having the composition $IL_1$-HT-ET, 67% TL-HT+33% BL-ET, Layer 7: intermediate layer $IL_2$-HT-ET, 67% TL-HT+ 33% BL-ET, Layer 8: reverse layer $R_5$ having the composition BL-ET, 100% BL-ET, Layer 9: reverse layer $R_6$ having the composition $IL_2$-HT-ET, 33% TL-HT+67% 15 BL-ET, Layer 10: bottom layer BL-ET, 100% BL-ET.

In a more preferred embodiment (exemplified in Example 2), the ten layers have the following compositions and thicknesses:

| Designation of the layer Layers | Thickness (mm) | Composition of the powder composition |
|---|---|---|
| TL-HT - top layer | 1-5 mm | 100% TL-HT |
| R1-IL1-HT-ET - reverse layer 1 | 0.6-1.2 mm | 67% TL-HT + 33% BL-ET |
| R2-TL-HT - reverse layer 2 | 0.6-1.2 mm | 100% TL-HT |
| ILi-HT-ET- intermediate layer 1 | 0.6-3 mm | 67% TL-HT + 33% BL-ET |
| R3-IL2-HT-ET - reverse layer 3 | 0.6-1.2 mm | 33% TL-HT + 67% BL-ET |
| R4-IL1-HT-ET - reverse layer 4 | 0.6-1.2 mm | 67% TL-HT + 33% BL-ET |
| IL2-HT-ET- intermediate layer 2 | 0.6-3 mm | 33% TL-HT + 67% BL-ET |
| R5-BL-ET - reverse layer 5 | 0.6-1.2 mm | 100% BL-ET |
| R6-IL2-HT-ET - reverse layer 6 | 0.6-1.2 mm | 33% TL-HT + 67% BL-ET |
| BL-ET - bottom layer | 1-25 mm | 100% BL-ET |

In another more preferred embodiment (exemplified in Example 2), the ten layers have the following compositions and thicknesses:

| Designation of the layer | Thickness (mm) | Composition of the powder composition |
|---|---|---|
| TL-HT - top layer | 1-5 mm | 100% TL-HT |
| R1-IL1-HT-ET - reverse layer 1 | 0.6-1.2 mm | 67% TL-HT + 33% BL-ET |
| R2-TL-HT - reverse layer 2 | 0.6-1.2 mm | 100% TL-HT |
| ILi-HT-ET- intermediate layer 1 | 0.8-3 mm | 67% TL-HT + 33% BL-ET |
| R3-IL2-HT-ET - reverse layer 3 | 0.8-1.2 mm | 33% TL-HT + 67% BL-ET |
| R4-IL1-HT-ET - reverse layer 4 | 0.8-1.2 mm | 67% TL-HT + 33% BL-ET |
| IL2-HT-ET- intermediate layer 2 | 0.8-3 mm | 33% TL-HT + 67% BL-ET |
| R5-BL-ET - reverse layer 5 | 0.8-1.2 mm | 100% BL-ET |
| R6-IL2-HT-ET - reverse layer 6 | 0.8-1.2 mm | 33% TL-HT + 67% BL-ET |
| BL-ET - bottom layer | 5-25 mm | 100% BL-ET |

In one embodiment (exemplified in Example 3), the multi-layered zirconia dental blank of the invention has thirteen layers arranged one on top of the other with 3 intermediate layers and 8 reverse layers:

Layer 1: top layer TL-HT, having a thickness from 1 mm to 5 mm,

Layer 2: reverse layer $R_1$ having the composition $IL_1$-HT-ET, having a thickness from 0.6 mm to 1.2 mm, Layer 3: reverse layer $R_2$ having the composition TL-HT, having a thickness from 0.6 mm to 1.2 mm, Layer 4: intermediate layer $IL_1$-HT-ET, having a thickness from 0.6 mm to 3 mm, Layer 5: reverse layer $R_3$ having the composition $IL_2$-HT-ET, having a thickness from 0.6 mm to 1.2 mm, Layer 6: reverse layer $R_4$ having the composition $IL_1$-HT-ET, having a thickness from 0.6 mm to 1.2 mm, Layer 7: intermediate layer $IL_2$-HT-ET, having a thickness from 0.6 mm to 3 mm, Layer 8: reverse layer $R_5$ having the composition $IL_3$-HT-ET, having a thickness from 0.6 mm to 1.2 mm, Layer 9: reverse layer $R_6$ having the composition $IL_2$-HT-ET, having a thickness from 0.6 mm to 1.2 mm, Layer 10: intermediate layer $IL_3$-HT-ET, having a thickness from 0.6 mm to 3 mm, Layer 11: reverse layer $R_7$ having the composition BL-ET, having a thickness from 0.6 mm to 1.2 mm, Layer 12: reverse layer $R_8$ having the composition $IL_3$-HT-ET, having a thickness from 0.6 mm to 1.2 mm, and Layer 13: bottom layer BL-ET, having a thickness from 1 mm to 25 mm.

In one embodiment (exemplified in Example 3), the multi-layered zirconia dental blank of the invention has thirteen layers arranged one on top of the other with 3 intermediate layers and 8 reverse layers:

Layer 1: top layer TL-HT, having a thickness from 1 mm to 5 mm,

Layer 2: reverse layer $R_1$ having the composition $IL_1$-HT-ET, having a thickness from 0.8 mm to 1.2 mm, Layer 3: reverse layer $R_2$ having the composition TL-HT, having a thickness from 0.8 mm to 1.2 mm, Layer 4: intermediate layer $IL_1$-HT-ET, having a thickness from 0.8 mm to 3 mm, Layer 5: reverse layer $R_3$ having the composition $IL_2$-HT-ET, having a thickness from 0.8 mm to 1.2 mm, Layer 6: reverse layer $R_4$ having the composition $IL_1$-HT-ET, having a thickness from 0.8 mm to 1.2 mm, Layer 7: intermediate layer $IL_2$-HT-ET, having a thickness from 0.8 mm to 3 mm, Layer 8: reverse layer $R_5$ having the composition $IL_3$-HT-ET, having a thickness from 0.8 mm to 1.2 mm, Layer 9: reverse layer $R_6$ having the composition $IL_2$-HT-ET, having a thickness from 0.8 mm to 1.2 mm, Layer 10: intermediate layer $IL_3$-HT-ET, having a thickness from 0.8 mm to 3 mm, Layer 11: reverse layer $R_7$ having the composition BL-ET, having a thickness from 0.8 mm to 1.2 mm, Layer 12: reverse layer $R_8$ having the composition $IL_3$-HT-ET, having a thickness from 0.8 mm to 1.2 mm, and Layer 13: bottom layer BL-ET, having a thickness from 5 mm to 25 mm.

In a particular preferred embodiment (exemplified in Example 3), the layers have the following powder compositions:

Layer 1: top layer TL-HT, 100% TL-HT

Layer 2: reverse layer $R_1$ having the composition $IL_1$-HT-ET, 75% TL-HT+25% BL-ET, Layer 3: reverse layer $R_2$ having the composition TL-HT, 100% TL-HT, Layer 4: intermediate layer $IL_1$-HT-ET, 75% TL-HT+25% BL-ET Layer 5: reverse layer $R_3$ having the composition $IL_2$-HT-ET, 50% TL-HT+50% BL-ET Layer 6: reverse layer $R_4$ having the composition $IL_1$-HT-ET, 75% TL-HT+25% BL-ET, Layer 7: intermediate layer $IL_2$-HT-ET, 50% TL-HT+50% BL-ET, Layer 8: reverse layer $R_5$ having the composition $IL_3$-HT-ET, 25% TL-HT+75% BL-ET, Layer 9: reverse layer $R_6$ having the composition $IL_2$-HT-ET, 50% TL-HT+50% 5 BL-ET, Layer 10: intermediate layer $IL_3$-HT-ET, having a thickness from 0.8 mm to 3 mm, 25% TL-HT+75% BL-ET, Layer 11: reverse layer $R_7$ having the composition BL-ET, 100% BL-ET Layer 12: reverse layer $R_8$ having the composition $IL_3$-HT-ET, 25% TL-HT+75% 10 BL-ET, and Layer 13: bottom layer BL-ET, 100% BL-ET.

In a more preferred embodiment (exemplified in Example 3), the thirteen layers have the following compositions and thicknesses:

| Designation of the layer | Thickness (mm) | Composition of the powder composition |
|---|---|---|
| TL-HT - top layer | 1-5 mm | 100% TL-HT |
| R1-IL1-HT-ET - reverse layer 1 | 0.6-1.2 mm | 75% TL-HT + 25% BL-ET |
| R2-TL-HT- reverse layer 2 | 0.6-1.2 mm | 100% TL-HT |
| IL1-HT-ET - intermediate layer 1 | 0.6-3 mm | 75% TL-HT + 25% BL-ET |
| R3-IL2-HT-ET - reverse layer 3 | 0.6-1.2 mm | 50% TL-HT + 50% BL-ET |
| R4-IL1-HT-ET - reverse layer 4 | 0.6-1.2 mm | 75% TL-HT + 25% BL-ET |
| IL2-HT-ET - intermediate layer 2 | 0.6-3 mm | 50% TL-HT + 50% BL-ET |
| R5-IL3-HT-ET - reverse layer 5 | 0.6-1.2 mm | 25% TL-HT + 75% BL-ET |
| R6-IL2-HT-ET - reverse layer 6 | 0.6-1.2 mm | 50% TL-HT + 50% BL-ET |
| IL3-HT-ET - intermediate layer 3 | 0.6-3 mm | 25% TL-HT + 75% BL-ET |
| R7-BL-ET - reverse layer 7 | 0.6-1.2 mm | 100% BL-ET |
| R8-IL3-HT-ET - reverse layer 8 | 0.6-1.2 mm | 25% TL-HT + 75% BL-ET |
| BL-ET - bottom layer | 1-25 mm | 100% BL-ET |

In another more preferred embodiment (exemplified in Example 3), the thirteen layers have the following compositions and thicknesses:

| Designation of the layer | Thickness (mm) | Composition of the powder composition |
|---|---|---|
| TL-HT - top layer | 1-5 mm | 100% TL-HT |
| R1-IL1-HT-ET - reverse layer 1 | 0.8-1.2 mm | 75% TL-HT + 25% BL-ET |
| R2-TL-HT- reverse layer 2 | 0.8-1.2 mm | 100% TL-HT |
| IL1-HT-ET - intermediate layer 1 | 0.8-3 mm | 75% TL-HT + 25% BL-ET |
| R3-IL2-HT-ET - reverse layer 3 | 0.8-1.2 mm | 50% TL-HT + 50% BL-ET |
| R4-IL1-HT-ET - reverse layer 4 | 0.8-1.2 mm | 75% TL-HT + 25% BL-ET |
| IL2-HT-ET - intermediate layer 2 | 0.8-3 mm | 50% TL-HT + 50% BL-ET |
| R5-IL3-HT-ET - reverse layer 5 | 0.8-1.2 mm | 25% TL-HT + 75% BL-ET |
| R6-IL2-HT-ET - reverse layer 6 | 0.8-1.2 mm | 50% TL-HT + 50% BL-ET |
| IL3-HT-ET - intermediate layer 3 | 0.8-3 mm | 25% TL-HT + 75% BL-ET |
| R7-BL-ET - reverse layer 7 | 0.8-1.2 mm | 100% BL-ET |
| R8-IL3-HT-ET - reverse layer 8 | 0.8-1.2 mm | 25% TL-HT + 75% BL-ET |
| BL-ET - bottom layer | 5-25 mm | 100% BL-ET |

In any of the embodiments described above, the order of the layers may be as described above or in reverse order.

Process for the Preparation of a Multi-Layered Zirconia Dental Blank of the Invention and Uses Thereof In another aspect, the invention relates to a process for the preparation of a multi-layered zirconia dental blank as described herein, comprising the steps of:

(a) putting the yttria-stabilized zirconia powder having the composition ET, the mixtures of the yttria-stabilized zirconia powder having the compositions $IL_X$-HT-ET, and the yttria-stabilized zirconia powder having the composition HT in layers on top of the other, or in reverse order, (b) pressing the yttria-stabilized zirconia powder layers to a green body, and 15 (c) pre-firing the green body to obtain the multi-layered zirconia dental blank.

The compositions HT and ET are typically provided in the form of powder batches, each powder comprising yttria-stabilized zirconia doped with colouring oxides.

In process step a), first, a layer of composition ET is filled into a mould. This layer corresponds to the bottom layer BL-ET. Then, the respective the mixtures of the yttria-stabilized zirconia powder having the compositions $IL_X$-HT-ET, ET and HT respectively, of the layers described herein are filled into the mould in 25 layers on top of the other. Finally, the yttria-stabilized zirconia powder having the composition HT is filled into the mould. The layering can be accomplished by using a scraper or a blade.

Alternatively, in process step a), first, a layer of composition HT is filled into a mould. This layer corresponds to the top layer TL-ET. Then, the respective the mixtures of the yttria-stabilized zirconia powder having the compositions IL$_x$-HT-ET, ET and HT respectively, of the layers described herein are filled into the mould in layers on top of the other. Finally, the yttria-stabilized zirconia powder having the composition ET is filled into the mould. The layering can be accomplished by using a scraper or a blade.

After each layering step a pressing step may be carried out to compact the respective powder composition.

Preferably, in process step b), a pressing step is carried out after all yttria-stabilized zirconia powders have been put in layers one on top of the other to obtain a green body of the multi-layered zirconia dental blank.

The L* value of the green body of the multi-layered zirconia dental blank of the invention is 99% or greater.

Compression is carried out at simple uniaxial pressures ranging from 50 MPa to 150 MPa, and additional postisostatic pressing with from 1,000 bar (100 MPa) to 4.0 bar (400 MPa). Preferably, pressures ranging from 70 MPa to 100 MPa biaxially and from 1,250 bar to 3,000 bar postisostatically are applied.

In process step (c), the green body is pre-sintered at temperatures ranging from 700° C. to 1,200° C., e.g. at temperatures ranging from 750° C. to 1,100° C., preferably from 800° C. to 1,000° C. to obtain the multi-layered zirconia dental blank.

The duration of the pre-firing, also designated as pre-sintering, at the temperatures described above ranges from 10 hour to 100 hours, e.g. from 15 hours to 90 hours, or from 20 hours to 80, or from 35 to 72 hours depending on the pre-firing temperature.

The multi-layered zirconia dental blank of the invention is provided, e.g. to the customer, in a preform suitable for use in a grinding machine, e.g. for use in a dental CAD/CAM machine, preferably of tooth-similar geometry, particularly preferred a dental milling block, a disc or a prefab.

Preforms, for example dental milling blocks, discs or prefabs, can be generated in any requested geometries. To make these preforms suitable for use in a grinding machine, e.g. for use in a dental CAD/CAM machine, a holder, for example a metal or polymer holder, can be fixed on the preform by common fixing techniques. The fixing of the preform includes but is not limited to using glue, e.g. a two-part epoxy glue.

In another aspect, the invention relates to a colored shaped ceramic blank as defined herein for the preparation of a dental article. Preferably, the dental article is a crown, a bridge, an inlay, an onlay, a veneer, a facing, a crown framework, a bridged framework, an implant, an abutment, a coping or an orthodontic appliance.

To produce a dental article or a dental restoration from a preform, e.g. for chair-side applications, any commercially available CAD/CAM milling machine may be used. The so obtained "crude" dental article or dental restoration may be finished by polishing the surface thereof. The "crude" dental article or dental restoration or a part thereof may also be treated with commercially available stain materials, glaze materials or veneering material.

The multi-layered zirconia dental blank of the invention may be provided, e.g. to the customer, with an instruction of use to form a kit of parts. The instruction of use may contain a description for what purpose the multi-layered zirconia dental blank is intended to be used, how the machining should be done and what sintering conditions should be applied. If desired, the kit of parts may further comprise sintering aids, a shade guide, polishing aids, colouring liquids or a combination thereof.

In another aspect, the present invention relates to the use of a multi-layered zirconia dental blank of the invention as described herein for the production of a dental article.

Dental articles include but are not limited to artificial teeth, inlays, onlays, bridges or crowns (including monolithic crowns), veneers, facings, crown frameworks, bridged frameworks, implants, abutments, copings or orthodontic appliances (e.g. brackets, buccal tubes, cleats and buttons) and parts thereof.

In another aspect, the invention relates to a process for producing a dental article, comprising the steps of:

(a) providing a multi-layered zirconia dental blank as defined above, (b) machining a pre-fired dental article out of the multi-layered zirconia dental blank as described above, and (c) sintering the pre-fired dental article to obtain the dental article as defined above.

To produce a dental article or a dental restoration from a preform, e.g. for chair-side applications, any commercially available CAD/CAM milling machine may be used in process step b). The so obtained "crude" dental article or dental restoration may be finished by polishing the surface thereof. The "crude" dental article or dental restoration or a part thereof may also be treated with commercially available stain materials, glaze materials or veneering material.

In process step c), the pre-fired dental article is sintered at typical temperatures ranging from 1,400° C. to 1,550° C., or at temperatures ranging from 1,450° C. to 1,500° C., from 1 to 15 hours or from 1 to 10 hours or from 1 to 5 hours or from 1 to 3 hours.

In another aspect, the invention relates to a dental article obtainable from the multi-layered zirconia dental blank of the invention as described herein.

The multi-layered zirconia dental blank of the invention as described herein is characterized by the gradients described above. After process step c) the colour gradient is visible. Surprisingly, in the dental article produced from the multilayered dental blank of the invention does not contain any perceptible boundaries of the intermediate layers. These are concealed by the reverse layers.

The dental article obtainable from the multi-layered zirconia dental blank of the invention can be characterized by one or more of the following features:

a) having a colour closely resembling a natural tooth without colour boundaries;

b) having a gradient of colour (L*a*b*) increasing from the top to the bottom, c) having a gradient of translucency, decreasing from the top to the bottom, d) having an gradient of yttria, increasing from the bottom to the top, e) having a gradient of strength decreasing from the bottom to the top, f) having a biaxial flexural strength in the range of 500 MPa to 1,500 MPa, and g) having a density from 5.5 g/cm3 to 6.1 g/cm$^3$ Any combinations of the embodiments of the invention described herein are considered to be within the scope of the invention.

The following Examples are merely specific embodiments of the present invention and are intended to illustrate but not to limit the invention.

EXAMPLES

1. Methods

1.1 Layer Thicknesses

Measurements of layer thicknesses can for example be made on cross-sections from a pre-sintered shaped body taken vertically with respect to the layering, by recording scaled photographic or microscopic images of these sections with a camera or a stereoscope and carrying out length measurements on these photographs, e.g., with the analySiS Five image-processing software or the ImageJ software. In particular, layer thickness means the average of several thicknesses determined for a layer.

1.2 Determination of Colour and Opacity

The $L^*a^*b^*$ and opacity values can be determined using a spectrometer (Konica Minolta CM-3610A). The measurement is performed on prepared polished plates with a diameter of 14 mm and a thickness of 1 mm of each layer, starting with the upper layer up to the bottom layer.

2. Starting Materials

For the preparation of a multi-layered zirconia dental blank of the invention the following powder compositions HT and ET were used. The compositions HT and ET are typically provided in the form of powder batches, each powder comprising yttria-stabilized zirconia doped with colouring oxides. The powder compositions ET-1 and ET-2 differ from each other in the content of yttria ($Y_2O_3$).

The compositions of the powder compositions ET and HT used as starting materials are shown in Table 2 below:

3. Preparation of a Multi-Layered Zirconia Dental Blank

General procedure: The multi-layered zirconia dental blanks of the invention were produced by using the powder compositions ET and HT, i.e. ET-1 and HT and ET-2 and HT respectively, described in section 2 above.

The powder composition BL-ET, i.e. BL-ET-1 or BL-ET-2, was filled first into a mould. Then, the respective the mixtures of the yttria-stabilized zirconia powders ET (ET-1 and ET-2) and HT corresponding to the compositions of the intermediate layers and the revers layers, respectively, of the layers described above were filled into the mould in layers on top of the other. Finally, the powder composition TL-HT was filled into the mould. A uniaxial pressure of 75 MPa and additionally a postisostatic pressure of 200 MPa was applied to the layered powders to yield a green body of the multi-layered zirconia dental blank. Thereafter the so obtained green body of the multi-layered zirconia dental blank was pre-fired at a temperature of 1000° C. for 72 hours.

As shown for Example 1, all multi-layered zirconia dental blanks of the Examples 1, 2 and 3 were prepared from ET-1 and HT and ET-2 and HT respectively.

TABLE 2

Composition of the powder composition ET (ET-1 and ET-2) and HT

| Component | Powder composition ET - Content of component (wt. %) | | Powder composition HT - Content of component (wt. %) |
|---|---|---|---|
| | ET-1 | ET-2 | |
| Tosoh powder | Zpex ® | Zpex ®4 | Zpex ®smile |
| Main crystal phase | Tetragonal | Tetragonal/cubic | Tetragonal/cubic |
| $ZrO_2$ + $HfO_2$ + $Y_2O_3$ + $Al_2O_3$ | (>99.9) | (>99.9) | (>99.9) |
| $HfO_2$ | <3 | <3 | <3 |
| $Y_2O_3$ (stabilizing crystal phase) | 4.65-5.95 (3 mol %) | 6.65-7.95 (4 mol %) | 8.55-10.11 (5 mol %) |
| $Al_2O_3$ | <0.1 | <0.1 | <0.1 |
| $SiO_2$ | <0.02 | <0.02 | <0.02 |
| $Fe_2O_3$ (incl. coloring component) | <0.12 | <0.12 | <0.12 |
| $Er_2O_3$ (coloring component) | 0-0.6 | 0-0.6 | 0-0.6 |
| $Co_3O_4$ or $MnO_2$ (coloring component) | 0.00007 | 0.00007 | 0.00007 |
| $ZrO_2$ | Remainder 90.1-92.25 | Remainder 88.1-90.25 | Remainder 85.9-88.35 |

3.1 Example 1—Multi-Layered Zirconia Dental Blank with 7 Layers

3.1.1 Example 1.1

A multi-layered zirconia dental blank with 7 layers, i.e. a top layer, 3 intermediate layers, 2 reverse layers and a bottom layer was prepared according to the general procedure described above:

Example 1.1A: Prepared from ET=ET-1 and HT:

| Designation of the layer | Thickness (mm) | Composition of the powder composition |
|---|---|---|
| TL-HT - top layer | 3 mm | 100% TL-HT |
| IL1-HT-ET - intermediate layer 1 | 1.3 mm | 75% TL-HT + 25% BL-ET-1 |
| IL2-HT-ET - intermediate layer 2 | 1.3 mm | 50% TL-HT + 50% BL-ET-1 |
| IL3-HT-ET - intermediate layer 3 | 1.3 mm | 25% TL-HT + 75% BL-ET-1 |
| R1-BL-ET - reverse layer 1 | 0.6 mm | 100% BL-ET-1 |
| R2-IL3-HT-ET - reverse layer 2 | 0.6 mm | 25% TL-HT + 75% BL-ET-1 |
| BL-ET - bottom layer | 8 mm | 100% BL-ET-1 |

Example 1.1B: Prepared from ET=FT-2 and HT

| Designation of the layer | Thickness (mm) | Composition of the powder composition |
|---|---|---|
| TL-HT - top layer | 3 mm | 100% TL-HT |
| ILi-HT-ET - intermediate layer 1 | 1.3 mm | 75% TL-HT + 25% BL-ET-2 |
| IL2-HT-ET - intermediate layer 2 | 1.3 mm | 50% TL-HT + 50% BL-ET-2 |
| IL3-HT-ET - intermediate layer 3 | 1.3 mm | 25% TL-HT + 75% BL-ET-2 |
| Ri-BL-ET - reverse layer 1 | 0.6 mm | 100% BL-ET-2 |
| R2-IL3-HT-ET - reverse layer 2 | 0.6 mm | 25% TL-HT + 75% BL-ET-2 |
| BL-ET - bottom layer | 8 mm | 100% BL-ET-2 |

3.1.2 Example 1.2

A multi-layered zirconia dental blank with 7 layers, i.e. a top layer, 3 intermediate layers, 2 reverse layers and a bottom layer was prepared according to the general procedure described above:

Example 1.2A: Prepared from ET=ET-1 and HT:

| Designation of the layer | Thickness (mm) | Composition of the powder composition |
|---|---|---|
| TL-HT - top layer | 3 mm | 100% TL-HT |
| ILi-HT-ET - intermediate layer 1 | 1.1 mm | 75% TL-HT + 25% BL-ET-1 |
| IL2-HT-ET - intermediate layer 2 | 1.1 mm | 50% TL-HT + 50% BL-ET-1 |
| IL3-HT-ET - intermediate layer 3 | 1.1 mm | 25% TL-HT + 75% BL-ET-1 |
| R1-BL-ET - reverse layer 1 | 0.8 mm | 100% BL-ET-1 |
| R2-IL3-HT-ET - reverse layer 2 | 0.8 mm | 25% TL-HT + 75% BL-ET-1 |
| BL-ET - bottom layer | 8 mm | 100% BL-ET-1 |

| Designation of the layer | Thickness (mm) | Composition of the powder composition |
|---|---|---|
| TL-HT - top layer | 3 mm | 100% TL-HT |
| ILi-HT-ET - intermediate layer 1 | 1.1 mm | 75% TL-HT + 25% BL-ET-2 |
| IL2-HT-ET - intermediate layer 2 | 1.1 mm | 50% TL-HT + 50% BL-ET-2 |
| IL3-HT-ET - intermediate layer 3 | 1.1 mm | 25% TL-HT + 75% BL-ET-2 |
| Ri-BL-ET - reverse layer 1 | 0.8 mm | 100% BL-ET-2 |
| R2-IL3-HT-ET - reverse layer 2 | 0.8 mm | 25% TL-HT + 75% BL-ET-2 |
| BL-ET - bottom layer | 8 mm | 100% BL-ET-2 |

3.1.3 Example 1.3

A multi-layered zirconia dental blank with 7 layers, i.e. a top layer, 3 intermediate layers, 2 reverse layers and a bottom layer was prepared according to the general procedure described above:

Example 1.3A: Prepared from ET=ET-1 and HT:

| Designation of the layer | Thickness (mm) | Composition of the powder composition |
|---|---|---|
| TL-HT - top layer | 3 mm | 100% TL-HT |
| ILi-HT-ET - intermediate layer 1 | 1.1 mm | 75% TL-HT + 25% BL-ET-1 |
| IL2-HT-ET - intermediate layer 2 | 1.1 mm | 50% TL-HT + 50% BL-ET-1 |
| IL3-HT-ET - intermediate layer 3 | 1.1 mm | 25% TL-HT + 75% BL-ET-1 |
| R1-BL-ET - reverse layer 1 | 0.8 mm | 100% BL-ET-1 |
| R2-IL3-HT-ET - reverse layer 2 | 0.8 mm | 25% TL-HT + 75% BL-ET-1 |
| BL-ET - bottom layer | 12 mm | 100% BL-ET-1 |

Example 1.3B: Prepared from ET=ET-2 and HT:

| Designation of the layer | Thickness (mm) | Composition of the powder composition |
|---|---|---|
| TL-HT - top layer | 3 mm | 100% TL-HT |
| IL1-HT-ET - intermediate layer 1 | 1.1 mm | 75% TL-HT + 25% BL-ET-2 |
| IL2-HT-ET - intermediate layer 2 | 1.1 mm | 50% TL-HT + 50% BL-ET-2 |
| IL3-HT-ET - intermediate layer 3 | 1.1 mm | 25% TL-HT + 75% BL-ET-2 |
| Ri-BL-ET - reverse layer 1 | 0.8 mm | 100% BL-ET-2 |
| R2-IL3-HT-ET - reverse layer 2 | 0.8 mm | 25% TL-HT + 75% BL-ET-2 |
| BL-ET - bottom layer | 12 mm | 100% BL-ET-2 |

3.1.4 Example 1.4

A multi-layered zirconia dental blank with 7 layers, i.e. a top layer, 3 intermediate 5 layers, reverse layers and a bottom layer was prepared according to the general procedure described above:

Example 1.4A: Prepared from ET=ET-1 and HT:

| Designation of the layer | Thickness (mm) | Composition of the powder composition |
|---|---|---|
| TL-HT - top layer | 3 mm | 100% TL-HT |
| ILi-HT-ET - intermediate layer 1 | 1.5 mm | 75% TL-HT + 25% BL-ET-1 |
| IL2-HT-ET - intermediate layer 2 | 1.0 mm | 50% TL-HT + 50% BL-ET-1 |
| IL3-HT-ET - intermediate layer 3 | 1.0 mm | 25% TL-HT + 75% BL-ET-1 |
| Ri-BL-ET - reverse layer 1 | 0.8 mm | 100% BL-ET-1 |
| R2-IL3-HT-ET - reverse layer 2 | 0.8 mm | 25% TL-HT + 75% BL-ET-1 |
| BL-ET - bottom layer | 12 mm | 100% BL-ET-1 |

Example 1.4B: Prepared from ET=ET-2 and HT:

| Designation of the layer | Thickness (mm) | Composition of the powder composition |
|---|---|---|
| TL-HT - top layer | 3 mm | 100% TL-HT |
| IL1-HT-ET - intermediate layer 1 | 1.5 mm | 75% TL-HT + 25% BL-ET-2 |
| IL2-HT-ET - intermediate layer 2 | 1.0 mm | 50% TL-HT + 50% BL-ET-2 |
| IL3-HT-ET - intermediate layer 3 | 1.0 mm | 25% TL-HT + 75% BL-ET-2 |
| R1-BL-ET - reverse layer 1 | 0.8 mm | 100% BL-ET-2 |
| R2-IL3-HT-ET - reverse layer 2 | 0.8 mm | 25% TL-HT + 75% BL-ET-2 |
| BL-ET - bottom layer | 12 mm | 100% BL-ET-2 |

3.2 Example 2—Multi-Layered Zirconia Dental Blank with 10 Layers

3.2.1 Example 2.1

A multi-layered zirconia dental blank with 10 layers, i.e. a top layer, 2 intermediate layers, 6 reverse layers and a bottom layer was prepared according to the general procedure described above:

| Designation of the layer | Thickness (mm) | Composition of the powder composition |
|---|---|---|
| TL-HT - top layer | 2 mm | 100% TL-HT |
| R1-IL1-HT-ET - reverse layer 1 | 0.6 mm | 67% TL-HT + 33% BL-ET |
| R2-TL-HT - reverse layer 2 | 0.6 mm | 100% TL-HT |
| IL1-HT-ET- intermediate layer 1 | 0.8 mm | 67% TL-HT + 33% BL-ET |
| R3-IL2-HT-ET - reverse layer 3 | 0.6 mm | 33% TL-HT + 67% BL-ET |
| R4-IL1-HT-ET - reverse layer 4 | 0.6 mm | 67% TL-HT + 33% BL-ET |
| IL2-HT-ET- intermediate layer 2 | 0.8 mm | 33% TL-HT + 67% BL-ET |
| R5-BL-ET - reverse layer 5 | 0.6 mm | 100% BL-ET |
| R6-IL2-HT-ET - reverse layer 6 | 0.6 mm | 33% TL-HT + 67% BL-ET |
| BL-ET - bottom layer | 5 mm | 100% BL-ET |

Example 2.1A: Prepared from ET=ET-1 and HT.
Example 2.1B: Prepared from ET=ET-2 and HT.

3.2.2 Example 2.2

A multi-layered zirconia dental blank with 10 layers, i.e. a top layer, 2 intermediate layers, 6 reverse layers and a bottom layer was prepared according to the general procedure described above:

| Designation of the layer | Thickness (mm) | Composition of the powder composition |
|---|---|---|
| TL-HT - top layer | 3 mm | 100% TL-HT |
| R1-IL1-HT-ET - reverse layer 1 | 0.6 mm | 67% TL-HT + 33% BL-ET |
| R2-TL-HT - reverse layer 2 | 0.6 mm | 100% TL-HT |
| IL1-HT-ET- intermediate layer 1 | 0.8 mm | 67% TL-HT + 33% BL-ET |
| R3-IL2-HT-ET - reverse layer 3 | 0.6 mm | 33% TL-HT + 67% BL-ET |
| R4-IL1-HT-ET - reverse layer 4 | 0.6 mm | 67% TL-HT + 33% BL-ET |
| IL2-HT-ET- intermediate layer 2 | 0.8 mm | 33% TL-HT + 67% BL-ET |
| R5-BL-ET - reverse layer 5 | 0.6 mm | 100% BL-ET |
| R6-IL2-HT-ET - reverse layer 6 | 0.6 mm | 33% TL-HT + 67% BL-ET |
| BL-ET - bottom layer | 12 mm | 100% BL-ET |

Example 2.2A: Prepared from ET=ET-1 and HT.
Example 2.2B: Prepared from ET=ET-2 and HT.

3.2.3 Example 2.3

A multi-layered zirconia dental blank with 10 layers, i.e. a top layer, 2 intermediate layers, reverse layers and a bottom layer was prepared 10 according to the general procedure described above:

| Designation of the layer | Thickness (mm) | Composition of the powder composition |
|---|---|---|
| TL-HT - top layer | 3 mm | 100% TL-HT |
| R1-IL1-HT-ET - reverse layer 1 | 0.8 mm | 67% TL-HT + 33% BL-ET |
| R2-TL-HT - reverse layer 2 | 0.8 mm | 100% TL-HT |
| IL1-HT-ET- intermediate layer 1 | 1.0 mm | 67% TL-HT + 33% BL-ET |
| R3-IL2-HT-ET - reverse layer 3 | 0.8 mm | 33% TL-HT + 67% BL-ET |
| R4-IL1-HT-ET - reverse layer 4 | 0.8 mm | 67% TL-HT + 33% BL-ET |
| IL2-HT-ET- intermediate layer 2 | 1.0 mm | 33% TL-HT + 67% BL-ET |
| R5-BL-ET - reverse layer 5 | 0.8 mm | 100% BL-ET |
| R6-IL2-HT-ET - reverse layer 6 | 0.8 mm | 33% TL-HT + 67% BL-ET |
| BL-ET - bottom layer | 10 mm | 100% BL-ET |

Example 2.3A: Prepared from ET=ET-1 and HT.
Example 2.3B: Prepared from ET=ET-2 and HT.

3.3 Example 3—Multi-Layered Zirconia Dental Blank with 13 Layers 3.3.1

Example 3.1

A multi-layered zirconia dental blank with 13 layers, i.e. a top layer, 3 intermediate layers, 8 reverse layers and a bottom layer was prepared according to the general procedure described above:

| Designation of the layer | Thickness (mm) | Composition of the powder composition |
|---|---|---|
| TL-HT - top layer | 3 mm | 100% TL-HT |
| R1-IL1-HT-ET - reverse layer 1 | 0.6 mm | 75% TL-HT + 25% BL-ET |
| R2-TL-HT- reverse layer 2 | 0.6 mm | 100% TL-HT |
| IL1-HT-ET - intermediate layer 1 | 0.6 mm | 75% TL-HT + 25% BL-ET |
| R3-IL2-HT-ET - reverse layer 3 | 0.6 mm | 50% TL-HT + 50% BL-ET |
| R4-IL1-HT-ET - reverse layer 4 | 0.6 mm | 75% TL-HT + 25% BL-ET |
| IL2-HT-ET - intermediate layer 2 | 0.6 mm | 50% TL-HT + 50% BL-ET |
| R5-IL3-HT-ET - reverse layer 5 | 0.6 mm | 25% TL-HT + 75% BL-ET |
| R6-IL2-HT-ET - reverse layer 6 | 0.6 mm | 50% TL-HT + 50% BL-ET |
| IL3-HT-ET - intermediate layer 3 | 0.6 mm | 25% TL-HT + 75% BL-ET |
| R7-BL-ET - reverse layer 7 | 0.6 mm | 100% BL-ET |
| R8-IL3-HT-ET - reverse layer 8 | 0.6 mm | 25% TL-HT + 75% BL-ET |
| BL-ET - bottom layer | 8 mm | 100% BL-ET |

Example 3.1A: Prepared from ET=ET-1 and HT.
Example 3.1B: Prepared from ET=ET-2 and HT.

3.3.2 Example 3.2

A multi-layered zirconia dental blank with 13 layers, i.e. a top layer, 3 intermediate layers, 8 reverse layers and a bottom layer was prepared according to the general procedure described above:

| Designation of the layer | Thickness (mm) | Composition of the powder composition |
|---|---|---|
| TL-HT - top layer | 4 mm | 100% TL-HT |
| R1-IL1-HT-ET - reverse layer 1 | 0.8 mm | 75% TL-HT + 25% BL-ET |
| R2-TL-HT- reverse layer 2 | 0.8 mm | 100% TL-HT |
| IL1-HT-ET - intermediate layer 1 | 0.8 mm | 75% TL-HT + 25% BL-ET |
| R3-IL2-HT-ET - reverse layer 3 | 0.8 mm | 50% TL-HT + 50% BL-ET |
| R4-IL1-HT-ET - reverse layer 4 | 0.8 mm | 75% TL-HT + 25% BL-ET |
| IL2-HT-ET - intermediate layer 2 | 0.8 mm | 50% TL-HT + 50% BL-ET |
| R5-IL3-HT-ET - reverse layer 5 | 0.8 mm | 25% TL-HT + 75% BL-ET |
| R6-IL2-HT-ET - reverse layer 6 | 0.8 mm | 50% TL-HT + 50% BL-ET |
| IL3-HT-ET - intermediate layer 3 | 0.8 mm | 25% TL-HT + 75% BL-ET |
| R7-BL-ET - reverse layer 7 | 0.8 mm | 100% BL-ET |
| R8-IL3-HT-ET - reverse layer 8 | 0.8 mm | 25% TL-HT + 75% BL-ET |
| BL-ET - bottom layer | 10 mm | 100% BL-ET |

Example 3.2A: Prepared from ET=ET-1 and HT.
Example 3.2B: Prepared from ET=ET-2 and HT.

3.3.3 Example 3.3

A multi-layered zirconia dental blank with 13 layers, i.e. a top layer, 3 intermediate layers, reverse layers and a bottom layer was prepared according to the general procedure described above:

| Designation of the layer | Thickness (mm) | Composition of the powder composition |
|---|---|---|
| TL-HT - top layer | 5 mm | 100% TL-HT |
| R1-IL1-HT-ET - reverse layer 1 | 1.0 mm | 75% TL-HT + 25% BL-ET |
| R2-TL-HT- reverse layer 2 | 1.0 mm | 100% TL-HT |
| IL1-HT-ET - intermediate layer 1 | 1.0 mm | 75% TL-HT + 25% BL-ET |
| R3-IL2-HT-ET - reverse layer 3 | 1.0 mm | 50% TL-HT + 50% BL-ET |
| R4-IL1-HT-ET - reverse layer 4 | 1.0 mm | 75% TL-HT + 25% BL-ET |
| IL2-HT-ET - intermediate layer 2 | 1.0 mm | 50% TL-HT + 50% BL-ET |
| R5-IL3-HT-ET - reverse layer 5 | 1.0 mm | 25% TL-HT + 75% BL-ET |
| R6-IL2-HT-ET - reverse layer 6 | 1.0 mm | 50% TL-HT + 50% BL-ET |
| IL3-HT-ET - intermediate layer 3 | 1.0 mm | 25% TL-HT + 75% BL-ET |
| R7-BL-ET - reverse layer 7 | 1.0 mm | 100% BL-ET |
| R8-IL3-HT-ET - reverse layer 8 | 1.0 mm | 25% TL-HT + 75% BL-ET |
| BL-ET - bottom layer | 10 mm | 100% BL-ET |

Example 3.3A: Prepared from ET=ET-1 and HT.
Example 3.3B: Prepared from ET=ET-2 and HT.

4. Preparation of a Sintered Multi-Layered Zirconia Dental Article

General procedure: A pre-fired dental article, i.e. a crown, was machined out of the pre-fired multi-layered zirconia dental blanks of the Examples described 10 above and sintered at a temperature of 1450° C. for 2 hours.

4.1 Examples 4.1A and 4.1B—Crown Prepared from a Multi-Layered Zirconia Dental Blanks with 13 Layers A crown was prepared from the pre-fired multi-layered zirconia dental blanks of the Examples 3.1A and 3.1B according to the general procedure described above described above and sintered at a temperature of 1450° C. for 2 hours. The blanks and crowns of Examples 4.1A and 4.1B show the following characteristic features:

| Feature | Example 4.1A | | | | Example 4.1B | | | |
|---|---|---|---|---|---|---|---|---|
| Colour closely resembling a natural tooth without colour boundaries | Yes | | | | Yes | | | |
| Gradient of colour (L*a*b*), increasing from the top to the bottom | | | Yes | | | | Yes | |
| | | L* | a* | b* | | L* | a* | b* |
| | TL | 88.10 | −2.14 | 13.60 | TL | 88.10 | −2.14 | 13.60 |
| | BL | 81.68 | 5.99 | 22.18 | BL | 83.37 | 5.27 | 23.68 |
| Gradient of translucency, decreasing from the top to the bottom | | Yes Opacity | | | | Yes Opacity | | |
| | TL | 69.04 | | | TL | 69.04 | | |
| | BL | 83.21 | | | BL | 77.00 | | |

-continued

| Feature | Example 4.1A | Example 4.1B |
|---|---|---|
| Gradient of yttria, increasing from the bottom to the top | Yes | Yes |

Figure 2:
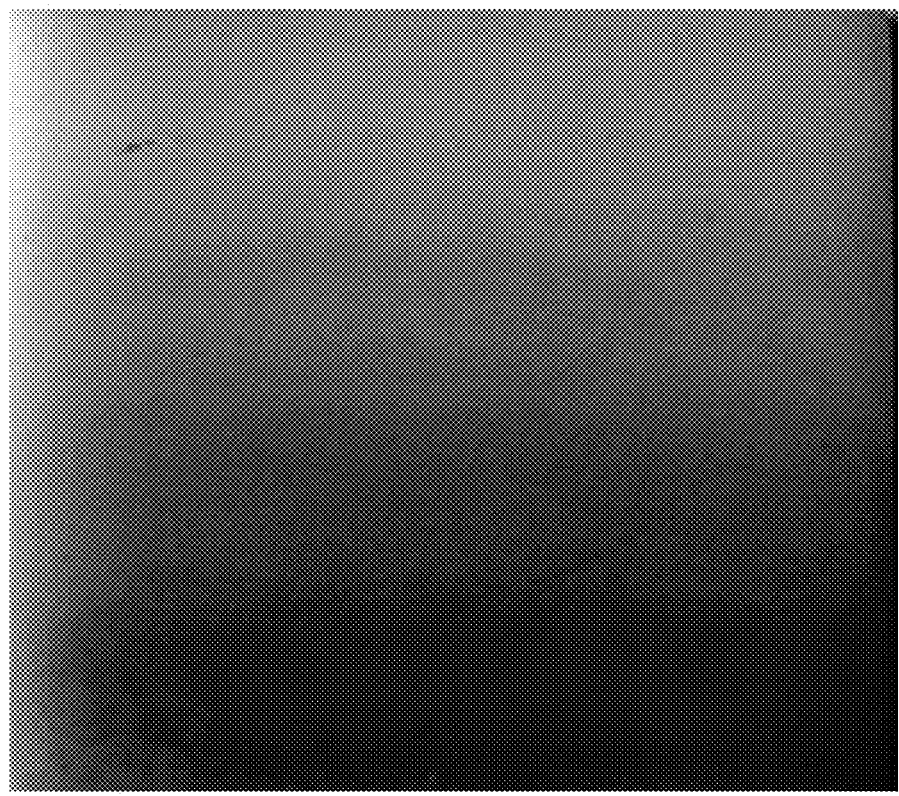
FIG. 2 shows a photo of a sintered multi-coloured zirconia ceramic of the state of the art with clearly perceptible boundaries of the intermediate layers produced from a multi-layered zirconia blank of the state of the art.
Figure 3:
FIG. 3 shows a photo of a sintered multi-coloured zirconia ceramic of the state of the art with clearly perceptible boundaries of the intermediate layers produced from a multi-layered zirconia blank of the state of the art.

FIGS. 2 and 3 show a photo of a sintered multi-coloured zirconia ceramic of the state of the art with clearly perceptible boundaries of the intermediate layers produced from a multi-layered zirconia blank of the state of the art.

Figure 4A:
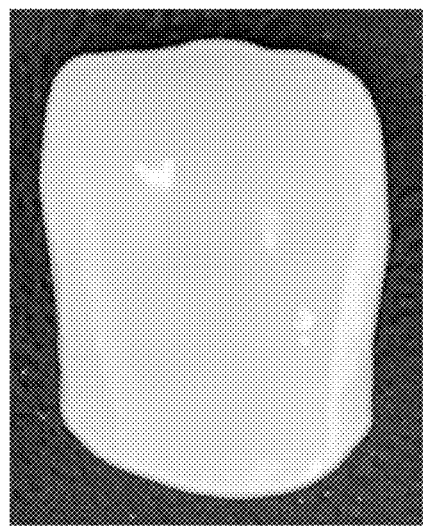
FIGS. 4A and 4B show a photo of a sintered multi-coloured zirconia dental article, i.e. of a crown, with imperceptible boundaries of the intermediate layers, produced from a multi-layered zirconia dental blank with 13 layers, as carried out in Examples 4.1A and 4.1 B.
Figure 4B:
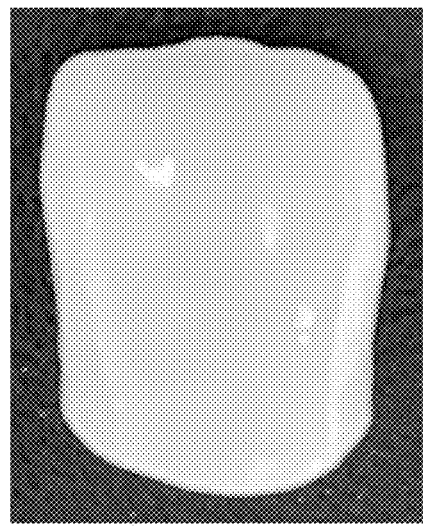

FIGS. 4A and 4B show a photo of a sintered multi-coloured zirconia dental article, i.e. of a crown, with imperceptible boundaries of the intermediate layers, produced from a multi-layered zirconia dental blank with 13 layers, as carried out in Examples 4.1A and 4.1B.

Figure 5A:
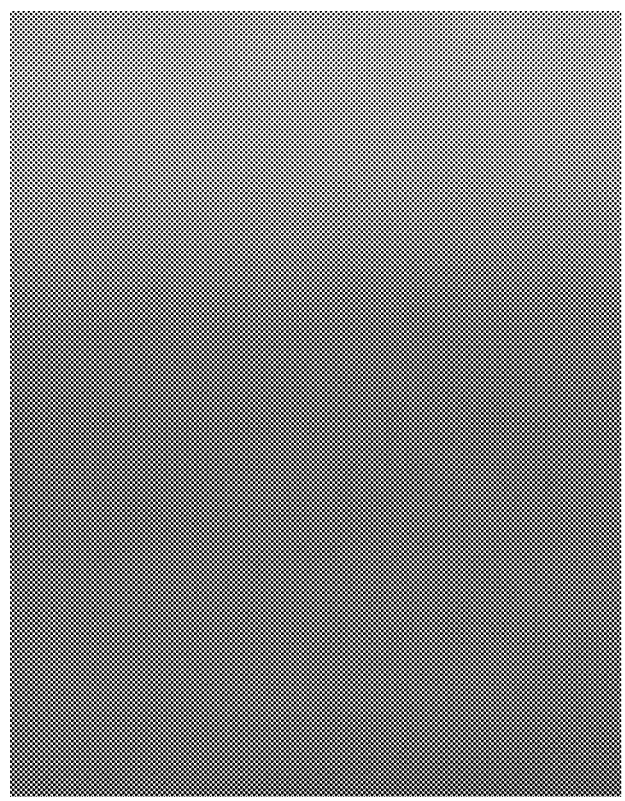
FIGS. 5A and 5B show a photo of an enlarged section of a sintered multicoloured zirconia dental article, i.e. of a crown, with imperceptible boundaries of the intermediate layers, produced from a multi-layered zirconia dental blank with 13 layers, as carried out in Examples 4.1A and 4.1B.
Figure 5B:
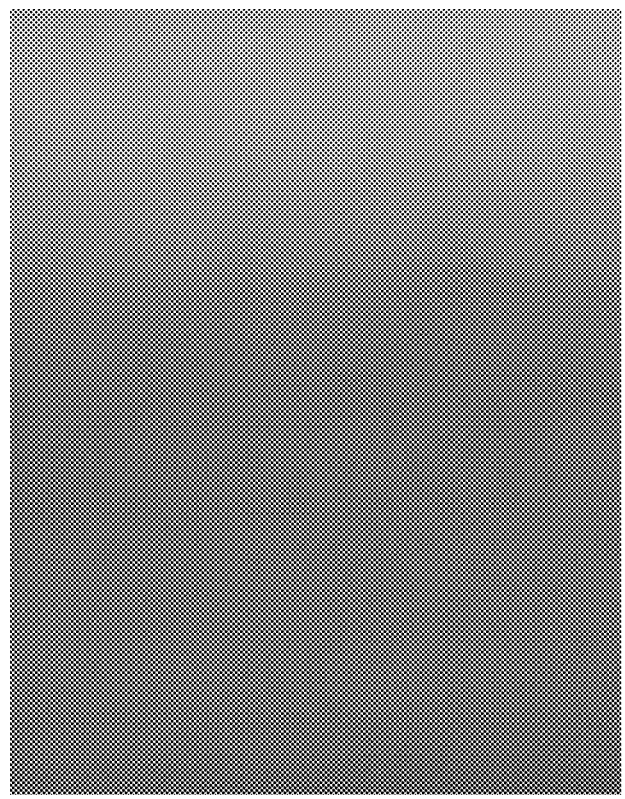

FIGS. 5A and 5B show a photo of an enlarged section of a sintered multi-coloured zirconia dental article, i.e. of a crown, with imperceptible boundaries of the intermediate layers, produced from a multi-layered zirconia dental blank with 13 layers, as carried out in Examples 4.1A and 4.1B.

Results

FIGS. 4A, 4B, 5A and 5B show that the 8 reverse layers $R_Y$ that are contained in the multi-layered zirconia dental blanks of the Examples 3.1A and 3.1B 20 effectively conceal the perceptible boundaries of the intermediate layers in the final multi-coloured zirconia ceramic, i.e. in the crown. Moreover, a crown produced from the multi-layered zirconia dental blank of the Examples 4.1A and 4.1B does not show any colour or translucency boundaries perceptible with the naked eye between the different layers, whereas the sintered multi-coloured 25 zirconia ceramic of the state of the art shown in FIGS. 2 and 3 have clearly perceptible boundaries of the intermediate layers.

The invention claimed is:

1. A multi-layered zirconia dental blank comprising:
   a top layer TL-HT having a composition TL-HT, the composition TL-HT comprising a composition HT, the composition HT comprising an yttria-stabilized zirconia powder,
   a bottom layer BL-ET having a composition BL-ET, the composition BL-ET comprising a composition ET, the composition ET comprising an yttria-stabilized zirconia powder,
   at least two intermediate layers $IL_X$-HT-ET comprising a mixture of the yttria-stabilized zirconia powders having the compositions TL-HT and BL-ET,
   X being an integer>1 designating the intermediate layer, wherein the yttria-stabilized zirconia powders having the compositions TL-HT and BL-ET comprise colouring oxides, and
   at least two reverse layers $R_Y$,
   Y being an integer>1 designating the reverse layer, and wherein
   the at least two reverse layers $R_Y$ are arranged in each case as a pair of reverse layers
   between the top layer TL-HT and a first intermediate layer $IL_1$-HT-ET, and/or
   between two intermediate layers $IL_X$-HT-ET, and/or
   between the last intermediate layer $IL_X$-HT-ET and the bottom layer BL-ET, and
   wherein each of the at least two reverse layers $R_Y$ has the same composition as the layer which is adjacent to the respective other reverse layer $R_Y$.

2. The multi-layered zirconia dental blank of claim 1, wherein the thickness of the layers is as follows:
   top layer TL-HT: from 1 mm to 5 mm,
   intermediate layers $IL_X$-HT-ET: from 0.6 to 5 mm,
   reverse layers $R_Y$: from 0.6 to 1.2 mm, and bottom layer BL-ET: from 1 mm to 25 mm.

3. The multi-layered zirconia dental blank of claim 1, having from 2 to 20 intermediate layers $IL_X$-HT-ET.

4. The multi-layered zirconia dental blank of claim 1, having from 2 to 44 reverse layers $R_Y$.

5. The multi-layered zirconia dental blank of claim 1, wherein the yttria composition HT of the top layer TL-HT contains from 8 wt. % to 30 wt. % yttria, and wherein the composition ET of the bottom layer BL-ET contains from 2 wt. % to 15 wt. % yttria.

6. The multi-layered zirconia dental blank of claim 1, wherein the zirconia dental blank comprises a reverse layer $R_1$ having the same composition as intermediate layer $IL_1$-HT-ET, and a reverse layer $R_2$ having the same composition as the top layer TL-HT.

7. The multi-layered zirconia dental blank of claim 1, wherein the zirconia dental blank comprises a reverse layer $R_Y$ having the same composition as the bottom layer BL-ET, and a reverse layer $R_{Y+1}$ having the same composition as the last intermediate layer $IL_X$-HT-ET.

8. The multi-layered zirconia dental blank of claim 1, having the following seven layers arranged one on top of the other:
   Layer 1: top layer TL-HT,
   Layer 2: intermediate layer $IL_1$-HT-ET having a composition $IL_1$-HT-ET,
   Layer 3: intermediate layer $IL_2$-HT-ET having a composition $IL_2$-HT-ET,
   Layer 4: intermediate layer $IL_3$-HT-ET having a composition $IL_3$-HT-ET,
   Layer 5: reverse layer $R_1$ having the composition BL-ET,
   Layer 6: reverse layer $R_2$ having the composition $IL_3$-HT-ET, and
   Layer 7: bottom layer BL-ET.

9. The multi-layered zirconia dental blank of claim 1, having the following ten layers arranged one on top of the other:
   Layer 1: top layer TL-HT,
   Layer 2: reverse layer $R_1$ having a composition $IL_1$-HT-ET,
   Layer 3: reverse layer $R_2$ having the composition TL-HT,
   Layer 4: intermediate layer $IL_1$-HT-ET,
   Layer 5: reverse layer $R_3$ having a composition $IL_2$-HT-ET,
   Layer 6: reverse layer $R_4$ having the composition $IL_1$-HT-ET;
   Layer 7: intermediate layer $IL_2$-HT-ET,
   Layer 8: reverse layer $R_5$ having the composition BL-ET,
   Layer 9: reverse layer $R_6$ having the composition $IL_2$-HT-ET, and
   Layer 10: bottom layer BL-ET.

10. The multi-layered zirconia dental blank of claim 1, having the following thirteen layers arranged one on top of the other:
    Layer 1: top layer TL-HT,
    Layer 2: reverse layer $R_1$ having a composition $IL_1$-HT-ET,
    Layer 3: reverse layer $R_2$ having the composition TL-HT,
    Layer 4: intermediate layer $IL_1$-HT-ET,
    Layer 5: reverse layer $R_3$ having a composition $IL_2$-HT-ET,
    Layer 6: reverse layer $R_4$ having the composition $IL_1$-HT-ET;
    Layer 7: intermediate layer $IL_2$-HT-ET, Layer 8: reverse layer $R_5$ having a composition $IL_3$-HT-ET,
Layer 9: reverse layer $R_6$ having the composition $IL_2$-HT-ET,
Layer 10: intermediate layer $IL_3$-HT-ET,
Layer 11: reverse layer $R_7$ having the composition BL-ET,
Layer 12: reverse layer $R_8$ having the composition $IL_3$-HT-ET, and
Layer 13: bottom layer BL-ET.

11. The multi-layered zirconia dental blank of claim 1, wherein the at least two reverse layers $R_Y$ interrupt the gradients of colour (L*a*b*), translucency, strength and yttria content within the top layer TL-HT and the bottom layer BL-ET and the intermediate layers $IL_X$-HT-ET.

12. The multi-layered zirconia dental blank of claim 1, wherein the colour becomes more intense (gradient of colour) and the translucency decreases (gradient of translucency) from the top layer TL-HT to the bottom layer BL-ET within the intermediate layers $IL_X$-HT-ET, being interrupted by the at least two reverse layers $R_Y$, and wherein the yttria content increases (gradient of yttria), and the strength decreases (gradient of strength) from the bottom layer BL-ET to the top layer TL-HT within the intermediate layers $IL_X$-HT-ET, being interrupted by the at least two reverse layers $R_Y$.

13. A process for the preparation of a multi-layered zirconia dental blank as defined in claim 1, comprising the steps of:
(a) putting the yttria-stabilized zirconia powder having the composition ET, the mixtures of the yttria-stabilized zirconia powder having the compositions $IL_X$-HT-ET, and the yttria-stabilized zirconia powder having the composition HT in layers on top of the other, or in reverse order,
(b) pressing the yttria-stabilized zirconia powder layers to a green body, and
(c) pre-firing the green body to obtain the multi-layered zirconia dental blank.

14. A process for producing a dental article, comprising the steps of:
(a) providing a multi-layered zirconia dental blank as defined in claim 1,
(b) milling a pre-fired dental article out of the multi-layered zirconia dental blank as defined in claim 1, and
(c) sintering the pre-fired dental article to obtain the dental article.

* * * * *